United States Patent [19]

Bare et al.

[11] Patent Number: 4,645,838

[45] Date of Patent: Feb. 24, 1987

[54] PYRAZOLOPYRIDINE COMPOUNDS, AND INTERMEDIATES, USEFUL AS ANXIOLYTIC AGENTS

[75] Inventors: Thomas M. Bare, West Chester; Anthony F. Heald, Glen Mills, both of Pa.

[73] Assignee: ICI Americas Inc., Wilmington, Del.

[21] Appl. No.: 624,530

[22] Filed: Jun. 25, 1984

Related U.S. Application Data

[62] Division of Ser. No. 485,191, Apr. 15, 1983, Pat. No. 4,511,568.

[30] Foreign Application Priority Data

May 12, 1982 [GB] United Kingdom ................. 8213700
Jan. 21, 1983 [GB] United Kingdom ................. 8301676

[51] Int. Cl.$^4$ .................. C07D 491/22; C07D 471/14
[52] U.S. Cl. ........................................ 546/84; 546/119
[58] Field of Search .................... 546/84, 119

[56] References Cited

U.S. PATENT DOCUMENTS 3,850,940 11/1974 Denzel et al. ...................... 546/119

Primary Examiner—Henry R. Jiles
Assistant Examiner—J. Richter
Attorney, Agent, or Firm—Rosemary M. Miano

[57] ABSTRACT

Compounds of the formula (I):

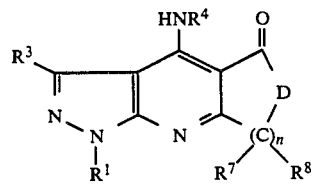

wherein $R^1$, $R^3$, $R^4$, $R^7$ and $R^8$ are as described herein, D is oxygen, n is 1 or 2 and the physiologically acceptable salts thereof useful in reducing anxiety in an animal such as man. The compounds are potent anxiolytics having reduced side effects compared to known anxiolytics. Also pharmaceutical compositions, intermediates and methods of treatment and synthesis are described.

6 Claims, No Drawings ns">PYRAZOLOPYRIDINE COMPOUNDS, AND INTERMEDIATES, USEFUL AS ANXIOLYTIC AGENTS This is a divisional of co-pending application Ser. No. 485,191 filed on Apr. 15, 1983, now U.S. Pat. No. 4,511,568, issued Apr. 16, 1985.

The present invention comprises certain lactones and lactams, their use as central nervous system depressants, methods for their preparation, pharmaceutical compositions containing them and intermediates used in their preparation. A chemical structure bearing some similarity to the lactones of the present invention is listed at the top of column 4 of U.S. Pat. No. 4,051,236 as an inhibitor of phosphodiesterase.

SUMMARY OF THE INVENTION

The compounds of the invention are pyrazolo[3,4-b]pyridine lactones and lactams. The invention compounds have been found to possess potent anxiolytic activity in animals with reduced side effects. For example, they are less sedating and show a lower propensity to potentiate alcohol at effective anxiolytic doses compared to known anxiolytics such as diazepam. Also part of the invention are pharmaceutical compositions containing one or more of the compounds for administration to an animal in need of an anxiety-reducing medication, such a method of treatment, methods for the synthesis of the compounds as well as novel intermediates used in the syntheses.

DETAILED DESCRIPTION OF THE INVENTION

The compounds of the invention are tricyclics of the following formula (I):

wherein
$R^1$ is alkyl, substituted alkyl, cycloalkyl, cycloalkylalkyl, alkenyl, alkynyl, aryl, substituted aryl, arylalkyl or (substituted aryl)alkyl;
$R^3$ is hydrogen or alkyl;
$R^4$ is hydrogen, alkyl, hydroxy-substituted alkyl, oxo-substituted alkyl, oxo-substituted alkyl substituted by an amino group, alkenyl, alkynyl, aryl, substituted aryl, arylalkyl, (substituted aryl)alkyl, aryl(oxo-substituted)alkyl or (substituted aryl)oxo-substituted alkyl;
D is oxygen or $NR^6$;
$R^6$ is hydrogen, alkyl, substituted alkyl, cycloalkyl, cycloalkylalkyl, alkenyl, alkynyl, aryl, substituted aryl, arylalkyl, (substituted aryl)alkyl or aryl(oxo-substituted)alkyl;
n is 1 or 2;
$R^7$ is hydrogen, alkyl, aryl, substituted aryl, arylalkyl or (substituted aryl)alkyl: and
$R^8$ is hydrogen, alkyl, aryl, substituted aryl, arylalkyl or (substituted aryl)alkyl;

and the pharmaceutically-acceptable acid-addition salts thereof.

$R^1$, in particular, is a straight or branched chain alkyl of about 1 to 10 carbons, or particularly about 3 to 7 carbons, e.g., n-pentyl, 1-, 2- or 3-methyl-n-butyl, 1- or 2-ethyl-n-butyl, n-hexyl, 1-, 2-, 3- or 4-methyl-n-pentyl, n-heptyl or n-octyl; a straight or branched chain alkyl of about 1 to 10 carbons, e.g., about 1 to 6 carbons, independently substituted by 1 or 2, preferably 1, hydroxy groups, alkoxy groups of about 1 to 6 carbons or oxo, e.g., keto, groups such as 4-hydroxy-n-pentyl or 4-oxo-n-pentyl or such an alkyl group substituted by at least one halogen, preferably a fluoro; a cycloalkyl of about 3 to 8 carbons, more particularly about 5 to 7 carbons, e.g., cyclohexyl; a cycloalkylalkyl of about 4 to 12 carbons, e.g., cyclopropylethyl; an alkenyl or alkynyl of about 3 to 10 carbons, such as from about 3 to 7 carbons, e.g., allyl, n-but-3-enyl or 2-methyl-prop-2-enyl; aryl of about 6 to 10 carbons, e.g., phenyl; aryl of about 6 to 10 carbons, particularly phenyl, independently substituted by 1 or more, particularly 1 or 2, of halogen, hydroxy, alkyl of about 1 to 6 carbons such as methyl, fluoro-substituted alkyl of about 1 to 6 carbons such as trifluoromethyl or alkoxy groups of about 1 to 6 carbons such as methoxy; arylalkyl of about 7 to 12 carbons, e.g., benzyl; or (substituted aryl)alkyl of about 6 to 10 carbons in the aryl, particularly phenyl, and about 1 to 4 carbons in the alkyl wherein the substitution is independently 1 or more, particularly 1 or 2, of halogen, hydroxy, alkyl of about 1 to 6 carbons such as methyl, fluoro-substituted alkyl of about 1 to 6 carbons such as trifluoromethyl or alkoxy groups of about 1 to 6 carbons such as methoxy. Preferably, the double or triple bond, if any, of $R^1$ is not on the carbon directly attached to nitrogen of the pyrazole ring. Further, the carbon of $R^1$ attached directly to the nitrogen of the pyrazole ring preferably has at least one hydrogen attached to it, e.g., it is a —CH$_2$— group.

$R^3$, in particular, is a hydrogen atom or a straight or branched chain lower alkyl of about 1 to 6 carbons, e.g., methyl.

$R^4$, in particular, is hydrogen: a straight or branched chain alkyl of about 1 to 10 carbons, more particularly about 1 to 6 carbons such as methyl, ethyl, n-propyl, iso-propyl and n-butyl: a hydroxy- or oxo-substituted alkyl, e.g., an aldehydo- or keto-substituted alkyl, of about 1 to 10 carbons, more particularly about 1 to 6 carbons such as 3-hydroxy-n-butyl, 4-oxo-n-butyl, 3-oxo-n-butyl, acetyl, propanoyl or butanoyl; an oxo-substituted alkyl of about 1 to 10 carbons substituted by an amino group, in particular an oxo adjacent to the —NH to form an alkanoyl which is substituted by —NR$^{17}$R$^{18}$ where R$^{17}$ and are independently hydrogen or alkyl of about 1 to 6 carbons: alkenyl or alkynyl of about 3 to 10 carbons, e.g., 3 to 7 carbons such as allyl, n-but-3-enyl or 2-methyl-prop-2-enyl; aryl of about 6 to 10 carbons, e.g., phenyl; aryl of about 6 to 10 carbons, particularly phenyl, independently substituted by 1 or more, particularly 1 or 2, of halogen, hydroxy, alkyl of about 1 to 6 carbons such as methyl, fluoro-substituted alkyl of about 1 to 6 carbons such as trifluoromethyl or alkoxy of about 1 to 6 carbons: arylalkyl of about 7 to 12 carbons, e.g., benzyl; (substituted aryl)alkyl of about 6 to 10 carbons in the aryl, particularly phenyl, and about 1 to 4 carbons in the alkyl wherein the substitution is independently 1 or more, particularly 1 or 2, of halogen, hydroxy, alkyl of about 1 to 6 carbons such as methyl, fluoro-substituted alkyl of about 1 to 6 carbons such as trifluoromethyl or alkoxy of about 1 to 6 carbons such as methoxy; aryl(oxo-substituted)alkyl of about 7 to 12 carbons such as benzoyl or phenylacetyl: or a (substituted aryl)oxo-substituted alkyl of about 6 to 10 carbons in the aryl, particularly phenyl, and about 1 to 4 carbons in the alkyl wherein the substitution is independently 1 or more, particularly 1 or 2, of halogen, hydroxy, alkyl of about 1 to 6 carbons such as methyl, fluoro-substituted alkyl of about 1 to 6 carbons such as trifluoromethyl or alkoxy groups of about 1 to 6 carbons such as methoxy with an example of the entire group being para-chlorobenzoyl.

D, in particular, is oxygen or $NR^6$.

$R^6$, in particular, is hydrogen; a straight or branched chain alkyl of about 1 to 10 carbons, more particularly about 1 to 6 carbons, e.g., methyl, ethyl, n-propyl, isopropyl, n-butyl, sec-butyl, iso-butyl, tert-butyl or n-pentyl: a straight or branched chain alkyl of about 1 to 10 carbons, e.g., about 1 to 6 carbons, independently substituted by 1 or 2, preferably 1, hydroxy groups, alkoxy groups of about 1 to 6 carbons or oxo, e.g., keto, groups, e.g., 2-hydroxy-n-propyl, 2-methoxyethyl, acetyl or 4-oxo-n-butyl, or such an alkyl group substituted by at least one halogen, e.g., a fluoro group, examples being 3,3,3-trifluoropropyl and 2,2,2-trifluoroethyl: a cycloalkyl of about 3 to 8 carbons, more particularly about 5 to 7 carbons, e.g., cyclohexyl: a cycloalkylalkyl of about 4 to 10 carbons, e.g., cyclopropylmethyl; an alkenyl or alkynyl of about 3 to 10 carbons, such as from about 3 to 6 carbons, e.g., allyl, n-but-3-enyl, 2-methylprop-2-enyl or 2-propynyl; aryl of about 6 to 10 carbons, e.g., phenyl or napthyl: aryl of about 6 to 10 carbons, particularly phenyl, independently substituted by one or more, particularly one or two, halogens, hydroxy groups, alkyl groups of about 1 to 6 carbons such as methyl, alkanoyl groups of about 1 to 6 carbons such as acetyl, alkoxy groups of about 1 to 6 carbons such as methoxy, halogenoalkyl groups containing fluoro, chloro, bromo or iodo atoms and about 1 to 6 carbons such as trifluoromethyl, nitro groups, cyano groups, alkoxy carbonyl groups of about 2 to 7 carbons such as methoxy carbonyl, amino groups and mono- and di-alkyl-substituted amino groups of about 1 to 12 carbons: arylalkyl of about 7 to 10 carbons, e.g., benzyl or phenethyl: (substituted aryl)alkyl of about 6 to 10 carbons in the aryl group, particularly phenyl, and about 1 to 4 carbons in the alkyl group wherein the substitution on the aryl group is independently one or more, particularly one or two, halogens, hydroxy groups, alkyl groups of about 1 to 6 carbons such as methyl, alkanoyl groups of about 1 to 6 carbons such as acetyl, alkoxy groups of about 1 to 6 carbons such as methoxy, halogenoalkyl groups of about 1 to 6 carbons such as trifluoromethyl, nitro groups, cyano groups, alkoxy carbonyl groups of about 2 to 7 carbons such as methoxy carbonyl, amino groups and mono- and di-alkyl-substituted amino groups of about 1 to 12 carbons: or aryl(oxo-substituted)alkyl of about 7 to 12 carbons such as benzoyl or phenylacetyl.

$R^7$ and $R^8$, in particular, are hydrogen; straight or branched chain lower alkyl, e.g., about 1 to 6 carbons, such as methyl, ethyl, n-propyl or n-butyl: aryl of about 6 to 10 carbons, e.g., phenyl: aryl of about 6 to 10 carbons, particularly phenyl, independently substituted by 1 or more, particularly 1 or 2, of halogen, hydroxy, alkyl of about 1 to 6 carbons such as methyl, fluoro-substituted alkyl of about 1 to 6 carbons such as trifluoromethyl or alkoxy of about 1 to 6 carbons such as methoxy: arylalkyl of about 7 to 12 carbons, e.g., benzyl: or (substituted aryl)alkyl of about 6 to 10 carbons in the aryl, particularly phenyl, and about 1 to 4 carbons in the alkyl wherein the substituion is independently 1 or more, particularly 1 or 2, of halogen, hydroxy, alkyl of about 1 to 6 carbons such as methyl, fluoro-substituted alkyl of about 1 to 6 carbons such as trifluoromethyl or alkoxy of about 1 to 6 carbons such as methoxy.

As used in the above description of various R groups, the term "halogen" is indicative of fluorine, chlorine, bromine and iodine atoms.

The pharmaceutically acceptable salts of the compounds of formula (I) are, for example, physiologically acceptable acid-addition salts such as mineral acid salts, e.g., hydrohalides, especially hydrochlorides and hydrobromides, sulfates, nitrates and phosphates.

Compounds of formula (I) and intermediates therefor may exist in the form of optical isomers, e.g., where $R^7$ is alkyl and $R^8$ is hydrogen or when an alkyl group is not symmetric such as 1-methyl-n-butyl, and geometric isomers, e.g., the cis and trans alkenyl groups. The present invention comprises all such optical and geometric isomers and racemates.

In particular, compounds of the invention are of the formula (I) wherein n is 1, i.e., of the following formula (II):

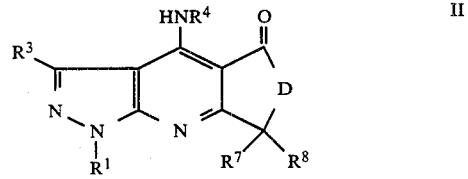

Particular values for $R^1$ are those of alkyl, cycloalkyl, cycloalkylalkyl, alkenyl, alkynyl or arylalkyl; for $R^4$ are those of hydrogen, alkyl, hydroxy-substituted alkyl, aldehydo-substituted alkyl or keto-, i.e., oxo-, substituted alkyl; for $R^6$ are those of hydrogen, alkyl, substituted alkyl, cycloalkyl cycloalkylalkyl, alkenyl, alkynyl, aryl, substituted aryl, arylalkyl or (substituted aryl)alkyl, e.g., hydrogen, alkyl, cycloalkyl, cycloalkylalkyl, alkenyl, alkynyl, aryl or arylalkyl: and for $R^7$ and $R^8$ are those of hydrogen or alkyl.

Preferred compounds of the formula (I) are 4-amino-6,7-dihydro-6-(2-methoxyethyl)-1-n-pentyl-pyrazolo[3,4-b]pyrrolo[3,4-e]pyridin-5(1H)-one and 4-amino-6,7-dihydro-1-(3-methyl-1-butyl)-6-n-propyl-pyrazolo[3,4-b]pyrrolo[3,4-e]pyridin-5(1H)-one and pharmaceutically-acceptable acid-addition salts thereof.

Particularly preferred compounds of the formula (I) are 4-amino-6,7-dihydro-1-n-pentyl-6-n-propyl-pyrazolo[3,4-b]pyrrolo[3,4-e]pyridin-5(1H)-one and pharmaceutically-acceptable acid-addition salts thereof.

The compounds, e.g., the intermediates, of the invention may be prepared by routes analogous to those described in U.S. Pat. No. 3,755,340 and more specifically as follows, the values of the various substituents being as described above for formula (I) unless otherwise indicated. An aminopyrazole of the following formula (III):

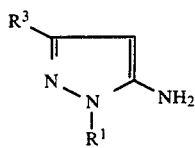

III is reacted, e.g., at a temperature of about 110° to 130° C. in the presence of poly-phosphoric acid, with an alkyl-carbonyl malonic acid diester of the following formula (IV):

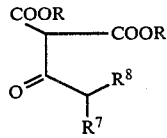

IV wherein R is alkyl such as lower alkyl, e.g., ethyl, to yield the intermediate of the following formula (V):

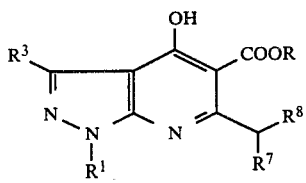

V

The starting material of formula (III) may be prepared as described in U.S. Pat. Nos. 3,414,580 and 3,755,340, by ring closure of an aldehyde or ketone hydrazone of the formula $R^{10}C=N-NH-CHR^3-CH_2CN$, wherein $R^{10}$ is the portion of $R^1$ other than the carbon which is directly attached to the nitrogen atom, e.g., if $R^1$ is n-pentyl, $R^{10}$ would be hydrogen and n-butyl: if $R^1$ is iso-propyl, $R^{10}$ would be two methyl groups: and if $R^1$ is cyclohexyl, $R^{10}$ would be pentylene. The starting material of formula (IV) may be prepared by methods generally described in Organic Synthesis, Coll. Vol. IV pages 285–288 (1963). For example, compounds of formula (IV) such as acetomalonic acid diethyl ester may be prepared by the reaction of an alkane acid chloride, e.g., acetyl chloride, with the anion of a dialkyl ester of malonic acid. For large scale preparations of the compounds of the invention, the compounds of formula (V) may be purified by conversion to a mineral acid salt, e.g., by reaction with hydrochloric or sulfuric acid, in a solvent such as butyl or ethyl acetate wherein the salt precipitates.

The compound of formula (V) may then be converted to a halo compound of the following formula (VI):

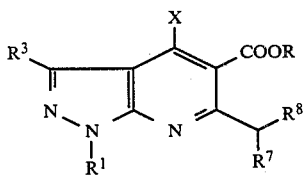

VI wherein X is chloro or bromo by reaction of (V) with a chlorinating or brominating agent such as phosphorus oxychloride, e.g., by reaction for 7 hours with 1½ equivalents of POCl₃ in a toluene solution at 90° C.

The compound of formula (VI) may be reacted with a peracid such as trifluoroperacetic acid or m-chloroperoxybenzoic acid to yield the corresponding N-oxide of the following formula (VII):

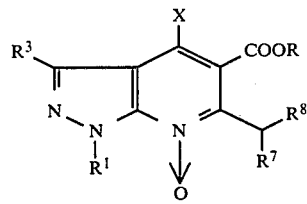

VII at a temperature of about 25° to 100° C., e.g., about 65° C., in an organic solvent such as a carboxylic acid, e.g., acetic acid. For large scale preparations, it is convenient to use m-chloroperoxybenzoic acid in toluene for 5 hours at about 45° C. after which the solution is washed with aqueous sodium bisulfite followed by sodium hydroxide followed by concentration to yield the starting material and N-oxide product. The N-oxide of formula (VII) is then reacted with a carboxylic acid anhydride of the formula $R^{11}COOCOR^{11}$ wherein $R^{11}$ is independently alkyl, e.g., of about 1 to 12 carbons, e.g., acetic anhydride, preferably in the presence of the corresponding acid, e.g., acetic acid, at a temperature of about 25° to 120° C., e.g., the reflux temperature of the acid, whereby a Polonovski-type rearrangement occurs to yield the carboxylate of the following formula (VIII):

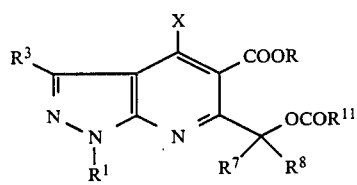

VIII wherein $R^{11}$ is as defined above.

Lactones of formula (II) wherein D is oxygen may be prepared from the carboxylate of formula (VIII) by reaction in an organic solvent such as toluene or ethanol at a temperature of about 25° to 130° C., with an amine of the formula $H_2NR^4$ to yield the lactone of the following formula (IX):

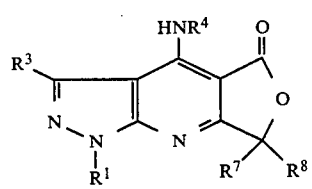

IX

The crude mixture of N-oxide (VII) and starting material (VI) may be processed through to the lactone of formula (IX) without purification of the intermediates: in which case the lactone (IX) is purified by crystallization from ethanol. Specific examples of lactones of formula (IX) which may be prepared are the following:

4-amino-1,7-dihydro-1-n-pentyl-5H-furo[3,4-b]pyrazolo[4,3-e]pyridin-5-one:

4-n-butylamino-1,7-dihydro-1-n-pentyl-5H-furo[3,4-b]pyrazolo[4,3-e]pyridin-5-one; and 4-amino-1-n-butyl-1,7-dihydro-5H-furo[3,4-b]pyrazolo[4,3-e]pyridin-5-one.

Lactams of the formula I wherein D is NR$^6$ may be prepared by reacting the lactone of formula (IX), preferably wherein at least one of R$^7$ and R$^8$ is hydrogen, with an amine of the formula H$_2$NR$^6$ in a solvent such as toluene, or the amine of formula H$_2$NR$^6$ may serve as its own solvent when present in molar excess. The reaction is conducted at high temperature and pressure, e.g., about 150° to 210° C. and in a pressure vessel to prevent loss of the amine of formula H$_2$NR$^6$, to yield the lactum of the following formula (X) with loss of H$_2$O:

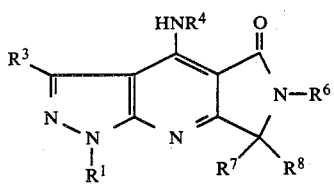

X

Specific examples of the lactams of formula (X) which may be prepared are the following:
6-allyl-4-amino-6,7-dihydro-1-n-pentylpyrazolo[3,4-b]pyrrolo[3,4-e]pyridin-5(1H)-one;
4-amino-6,7-dihydro-1-n-pentyl-6-n-propyl-pyrazolo[3,4-b]pyrrolo[3,4-e]pyridin-5(1H)-one; and
4-amino-6-n-butyl-6,7-dihydro-1-n-pentylpyrazolo[3,4-b]pyrrolo[3,4-e]pyridin-5(1H)-one.

The salts of compounds of formula (I) are prepared in conventional manner, e.g., by mixing solutions of the desired acid with the formula (I) compound in diethylether, and collecting the precipitate.

Further, compounds of formula (I) wherein R$^6$ is other than hydrogen may be prepared by reacting a compound of formula (I) wherein R$^6$ is hydrogen with the appropriate agent, e.g., an alkylating agent such as an alkyl bromide. Thus, when R$^6$ is hydrogen in formula (I), a compound of formula (I) wherein R$^6$ is a substituted alkyl group such as phenethyl, an alkenyl group or an alkynyl group may be obtained by producing the lactam anion, e.g., with a strong base such as sodium hydride, and reacting the anion with the corresponding alkylating, alkenylating or alkynylating agent, e.g., an alkyl halide. This reaction may be carried out when R$^4$ is other than hydrogen to obtain the desired mono-substituted lactam. When R$^4$ is hydrogen, the reaction should be monitored closely to detect disubstituted materials, e.g., where the alkylation also occurs at the R$^4$ position. If a mixture of products is obtained, such may be separated by standard techniques, e.g., by high pressure liquid chromatography. When R$^4$ is hydrogen and R$^6$ is other than hydrogen, substitution at the R$^4$ position may be carried out in a similar manner, i.e., by reaction with a strong base such as sodium hydride and subsequent reaction with an R$^4$-halogen compound where such R$^4$ is other than hydrogen.

In addition, compounds of formula (I) wherein R$^4$ is keto-substituted alkyl and the keto group is at the 1-position of the alkyl, i.e., an oxo group to form an amide, may be obtained by acylating a compound of formula (I) wherein R$^4$ is hydrogen with an anhydride such as acetic anhydride with a catalyst such as 4-dimethylaminopyridine. If a compound of formula (I) wherein R$^4$ and/or R$^6$ is hydrogen is desired, the corresponding substituted compound may be reduced down to hydrogen, e.g., by hydrogenation of the corresponding benzyl group. In addition, if R$^1$, R$^3$, R$^4$, R$^6$, R$^7$ and/or R$^8$ in formula (I) is a saturated group, the desired compound may be made by reduction of the corresponding unsaturated compound, e.g., by hydrogenation of an alkenyl group.

In a second general reaction scheme to produce the compounds of the invention, particularly those wherein R$^7$ and/or R$^8$ are other than hydrogen, the aminopyrazole of the formula (III) is reacted with a dialkylalkoxy methylene malonate of the formula (R$^{12}$OOC)$_2$C=CHOR$^{12}$, wherein R$^{12}$ is independently alkyl, e.g., alkyl of about 1 to 6 carbons, to produce an enamine of the following formula (XI):

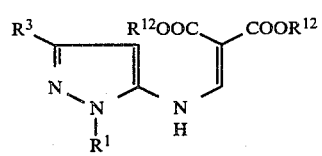

XI with loss of 1 mole of alkanol by heating to an elevated temperature, e.g., over 100° C. The 6-membered pyridine ring is then formed by heating the formula (XI) compound neat or in a solvent, e.g., over about 200° C., to yield the compound of the following formula (XII):

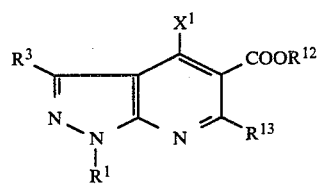

XII wherein X$^1$ is hydroxy and R$^{13}$ is hydrogen; which is then converted to the compound of formula (XII) wherein X$^1$ is a halogen and R$^{13}$ is hydrogen, by reaction with a halogenating agent such as phosphorus oxychloride under reflux. The corresponding N-oxide at the pyridine nitrogen may then be prepared by oxidation with an agent such as hydrogen peroxide, trifluoroperacetic or m-chloroperoxybenzoic acid by reaction at about 0° to 110° C. From the halo N-oxide, the halo group is converted to an ether N-oxide of the formula (XIIA):

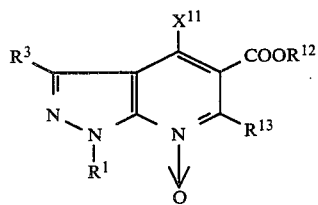

XIIA wherein X$^{11}$ is alkoxy, e.g., of about 1 to 6 carbons, R$^{12}$ is alkyl and R$^{13}$ is hydrogen by reaction with the corresponding alkoxide at about room temperature or somewhat lower. The ether N-oxide is then converted to the compound of formula (XII) wherein X$^1$ is alkoxy, R$^{12}$ is alkyl and R$^{13}$ is bromo or iodo by reaction with a halogenating agent such as phosphorus oxybromide at a temperature of about 30° to 100° C., e.g., at reflux in a solvent such as chloroform, the oxide of the N-oxide having been removed by the conditions of the reaction. The thus-produced halo compound is converted to a lithium adduct by reaction with an alkyl lithium compound such as n-butyl lithium at a temperature of about −80° to −120° C., the adduct being of the formula (XII) wherein X is alkoxy, $R^{12}$ is alkyl and $R^{13}$ is a lithium atom. The lithium adduct need not be isolated but may reacted in situ at the low temperature of formation with an aldehyde such as acetaldehyde or benzaldehyde, or if $R^7$ and $R^8$ are both to be other than hydrogen, with a ketone such as acetone, to yield directly the compound of structure (IX) wherein the $HNR^4$ group is replaced by an alkoxy group, which compound is then reacted with ammonia or another $H_2NR^4$ compound at a temperature of about 25° to 100° C., e.g., in a solvent or neat with liquid ammonia in a steel bomb at room temperature or a higher temperature if a solvent is used to produce the lactone of formula (IX), e.g., wherein $R^4$ is hydrogen. The lithium adduct of the formula (XII) wherein $X^1$ is alkoxy, $R^{12}$ is alkyl and $R^{13}$ is a lithium atom may, instead of being reacted with an aldehyde or ketone to produce a 5-membered lactone, be reacted with an epoxide of the formula to produce a 6-membered lactone, e.g., by reaction at about −80° to −120° C. in an inert solvent such as THF or hexane.

In a third general reaction scheme to produce the compounds of the invention of formula (I) wherein n is 1 or 2 and particularly for compounds wherein D is $NR^6$, a 4-cyano pyrazole of the following formula (XIII)

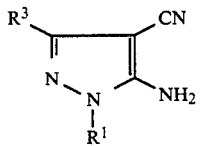   XIII is produced by reacting a hydrazine of the formula $R^1$—NH—$NH_2$ with an alkoxymethylenemalononitrile of the formula $(R^{14}O)R^3C=C(CN)_2$ at about 40° to 80° C. in a solvent such as an alcohol, e.g., ethanol. The synthesis of such 4-cyano pyrazoles is described in U.S. Pat. No. 3,732,225. The 4-cyano pyrazole may then be condensed with a 2,4-diketo heterocycle of 5 or 6 members of the following formula (XIV) to yield an enamine of the following formula (XV)

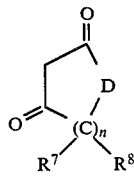   XIV

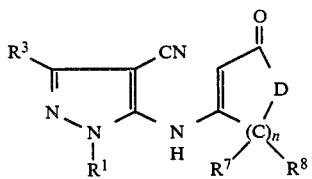   XV wherein $R^1$, $R^3$, D, n, $R^7$ and $R^8$ are as described above, it being understood that the two $R^7$ and two $R^8$ groups when n is 2 may be independently chosen from each other although preferably only one or two of the 4 possible $R^7$ and $R^8$ groups are other than hydrogen. The condensation reaction may take place at about 75° to 150° C. with loss of water in a solvent such as toluene with an enamine promoter such as p-toluenesulfonic acid.

For the synthesis of a 2,4-diketopyrrolidine or a 2,4-diketotetrahydrofuran of the formula (XIV) wherein n is 1, $H_2D$ is condensed with an alpha-bromoester of the formula $CH_3CH_2OCOCR^7R^8Br$ at about 0° C. in a solvent such as methylene chloride to yield an adduct of the formula $CH_3CH_2OCOCR^7R^8DH$ which is then reacted with ethyl malonyl chloride of the formula $ClCOCH_2COOCH_2CH_3$ in the presence of potassium carbonate at about 0° C. to yield an adduct of the formula $CH_3CH_2OCOCR^7R^8DCOCH_2COOCH_2CH_3$. The thus-produced adduct undergoes internal cyclization in the presence of sodium methoxide in methanol with toluene as a cosolvent at about 90°–110° C. to produce a 2,4-diketopyrrolidine or a 2,4-diketotetrahydrofuran of the formula (XIV) wherein n is 1 and one of the hydrogens between the two oxo groups is replaced by a —$COOCH_3$ group. From the —$COOCH_3$ substituted compound, the compound of formula (XIV) wherein n is 1, may be produced by heating to reflux in a solvent such as acetonitrile to effect decarbomethoxylation. The synthesis of such compounds, also known as tetramic and tetronic acids, is also described by T. P. C. Mulholland et al. in the Journal of the Chemical Society, Perkin Transactions I, pages 2121–2128 (1972): by G. Lowe et al. in the Journal of the Chemical Society, Perkin Transactions I, pages 2907–2910 (1973): and by V. J. Lee et al. in the Journal of the American Chemical Society, Vol. 100, pages 4225–4239 (1978).

For the synthesis of the 6-membered heterocycles of formula (XIV), analogous reactions are used. Thus, to prepare 2,4-diketopiperidines of the formula (XIV) where n is 2, a malonamide of the formula $CH_3CH_2OOC—CH_2CO—NR^6—(CR^7R^8)_2—COOCH_3$ is cyclized by heating to reflux in benzene with added sodium methoxide followed by dealkoxycarboxylation by heating in acetonitrile as described by S. Toda et al. in the Journal of Antibiotics, Volume XXXIII, No. 2, pages 173–181 (1980). For the corresponding 2,4-diketopyrans of the formula (XIV) wherein n=2 and D=O, reaction of ethyl 3-hydroxypropanoates of the formula $CH_3CH_2OCO(CR^7R^8)_2OH$ with ethyl malonyl chloride of the formula $ClCOCH_2COOCH_2CH_3$ in the presence of aqueous potassium carbonate at about 0° C. yields a product of the formula $CH_3CH_2OCO(CR^7R^8)_2OCOCH_2COOCH_2CH_3$. This product is cyclized in the presence of a sodium alkoxide such as sodium methoxide in methanol with toluene as a cosolvent at about 90°–110° C. to afford a 2,4-diketopyran of the formula (XIV) wherein n=2, D=O, and one of the hydrogens between the two oxo groups is replaced by a —$COOCH_3$ group. Subsequent refluxing in a solvent such as acetonitrile effects decarbomethoxylation to produce 2,4-dioxooxanes of the formula (XIV) wherein n=2 and D=O. 2,4-Diketopyran, also known as 4-hydroxy5,6-dihydro-2H-pyran-2-one, is described by K. Miyazaki in Chemical Abstracts, Vol. 82, 134452a (1975) and Vol. 84, 61517e (1976). The enamine of the formula (XV) is then cyclized internally by reaction between the cyano group and the activated carbon which is alpha to the oxo group to produce a compound of formula (I) wherein $R^4$ is hydrogen. Such an internal cyclization may take place in the presence of $ZnCl_2$ as a reaction promoter at an elevated temperature greater than about 150° C., e.g., about 150° to 250° C., neat or in the presence of a high boiling solvent such as xylene or chlorobenzene, or in the initial presence of a solvent to facilitate transfer of starting material. The use of ZnCl₂ as a reaction promoter to form a 4-aminopyridine is described by J. A. Moore et al. in Tetrahedron Letters, No. 20, pages 1277-1281 (1963).

The compounds of the invention of formula (I) wherein n is 2, i.e., 6-membered lactones and lactams may also be prepared by first converting an hydroxy compound of formula (V) to the corresponding ether by reaction with an alkyl iodide of the formula $R^{15}I$ wherein $R^{15}$ is alkyl, e.g., of 1 to 6 carbons, in the presence of potassium carbonate at about 70° C. in a solvent such as DMF, acetone or methyl ethyl ketone or by reaction of a halo compound of formula (VI) with an alkoxide anion of the formula $R^{15}O^-$ at reflux in the corresponding alcohol. A lithium adduct of the ether, i.e., wherein the hydrogen directly attached to the carbon bonded to both $R^7$ and $R^8$ is replaced by lithium, is then prepared by reaction with lithium diisopropylamide at about −78° C. in THF. The lithium adduct may be reacted, without isolation, with carbon dioxide, an $R^7$CHO aldehyde or an $R^7COR^8$ ketone wherein $R^7$ and $R^8$ are other than hydrogen at a temperature of about −50° to −80° C. to yield a compound of the following formula (XVI)

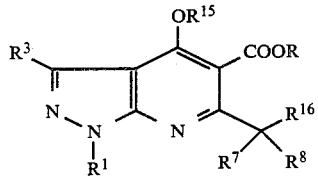
XVI wherein is —COOH if CO₂ was the reagent or if an aldehyde or ketone was the reagent. If $R^{16}$ is —COOH, the compound must be converted to the alcohol by reduction with a reducing agent such as a borane methyl sulfide complex initially at a temperature of 0° C. to the reflux temperature of THF. Other reducing agents suitable for the selective reduction of carboxylic acids to alcohols may be used. The compound of formula (XVI) wherein $R^{16}$ is —$CR^7R^8OH$ may be cyclized to the lactone with replacement of the —$OR^{15}$ group by a —NH₂ group, by reaction with liquid NH₃ in a steel pressure vessel at about 100° C. The thus-produced 6-membered lactone may be converted to the corresponding lactam as described previously by reaction with an amine of the formula $R^6NH_2$.

Although the three general synthesis methods described above for the compounds of the invention provide the $R^1$ group at an early stage of synthesis, i.e., use of an aldehyde of the formula $R^{10}$—CHO, or a hydrazine of the formula $R^1$—NH—NH₂, it is possible to provide the $R^1$ group at a later stage by converting a compound of formula (VI) to one wherein $R^1$ is H by reaction with N-bromosuccinimide in a solvent such as CCl₄ under reflux. The reaction mixture is preferably illuminated with a sunlamp. The compounds of formula (VI) wherein $R^1$ is H may then be reacted with a compound of the formula $R^1$—Br where $R^1$ is other than hydrogen, to produce a compound of formula (VI) with a new $R^1$ substituent as shown in the following examples. The reaction with $R^1$—Br may be conducted at about room temperature in the presence of a molar excess of a base such as potassium carbonate. Compounds of the formula $R^1$—Br may be prepared as known in the art, e.g., by preparation of $R^1$—OH from the corresponding carboxylic acid by reduction with lithium aluminum hydride and bromination of $R^1$—OH with triphenylphosphine and bromine. If $R^4$ is to be other than hydrogen, the —NH₂ derivative may be reacted as described above, e.g., reaction with sodium hydride followed by an $R^4$-halogen compound or by reaction with an acylating agent where $R^4$ is a 1-oxoalkyl derivative or by nucleophilic displacement of one HNR⁴ group by another at 250° to 300° C. with $R^4NH_2$ with conversion of the lactone to the lactam if at least one of $R^7$ and $R^8$ are hydrogen.

According to a further feature of the invention there is provided a process for the preparation of the compounds of the formula (I), wherein $R^1$, $R^3$, $R^4$, D, n, $R^6$, $R^7$ and $R^8$ are as stated above unless otherwise stated, and pharmaceutically-acceptable acid-addition salts thereof, which comprises:

(a) in the case where D is oxygen and n is 1, cyclizing a compound of the following formula (VIII):

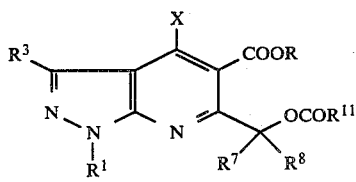
VIII wherein X is chloro or bromo and R and $R^{11}$, which may be the same or different, are alkyl, by reacting it with an amine of the formula $H_2NR^4$ at a temperature of 25° to 130° C.;

(b) in the case where D is oxygen, reacting a compound of the following formula (XVII):

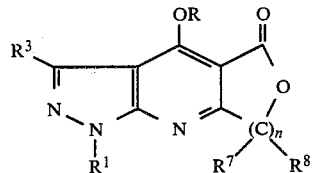
XVII with an amine of the formula $H_2NR^4$;

(c) in the case where $R^4$ is hydrogen, internally cyclizing a compound of the following formula (XV)

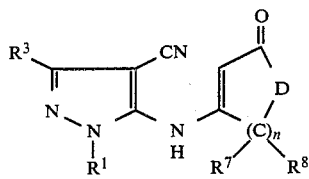
XV at a temperature of 150° to 250° C.;

(d) in the case where D is $NR^6$, reacting a compound of the formula (I), wherein D is oxygen, with an amine of the formula $H_2NR^6$;

(e) in the case where D is $NR^6$ and $R^6$ is other than hydrogen, reacting a compound of the formula (I), wherein D is NH, with a compound of the formula $R^6$—LG, wherein LG is a leaving group, in the presence of a strong base;

(f) in the case where $R^4$ is alkanoyl, aroyl, arylalkanoyl or (substituted aryl)alkanoyl, acylating a compound of the formula (I) wherein $R^4$ is hydrogen by reacting it with the appropriate acyl halide or acid anhydride;

(g) in the case where D is oxygen and n is 2, cyclizing a compound of the following formula (XVI):

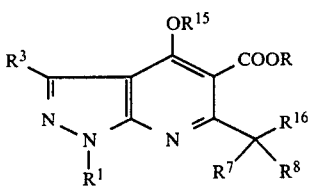

wherein $R^{15}$ is alkyl and $R^{16}$ is —$CR^7R^8OH$, by reacting it with an amine of the formula $H_2NR^4$;

(h) in the case where D is oxygen, $R^4$ is other than hydrogen, and at least one of $R^7$ and $R^8$ is other than hydrogen, reacting a compound of the formula (I), wherein $R^4$ is hydrogen, with an amine of the formula $H_2NR^4$ wherein $R^4$ is other than hydrogen, at 250° to 300°; or (i) in the case where $R^4$ is other than hydrogen, reacting a compound of the formula (I), wherein $R^4$ is hydrogen, with a compound of the formula $R^4$-LG, wherein $R^4$ is other than hydrogen and LG is a leaving group, in the presence of a strong base.

The compounds of this invention of the formula (I) are useful in the suppression of central nervous system activity in mammals, e.g., in humans, by the suppression of convulsions, the relaxation of skeletal muscles, by inducing sleep, and particularly for the treatment of anxiety.

The pharmaceutical compositions of the invention may be prepared and used according to methods known for the compounds cartazolate and tracazolate. Specifically, the new compounds of this invention are central nervous system depressants and may be used as tranquilizers or ataractic agents for the relief of anxiety and tension states, for example, in mice, cats, rats, dogs and other mammalian species such as man, in the same manner as chlordiazepoxide. For this purpose a compound or mixture of compounds of formula (I), or non-toxic physiologically acceptable acid addition salts thereof, may be administered orally or parenterally in a conventional dosage form such as tablet, pill, capsule, injectable or the like. The dosage in mg/kg of body weight of compounds of the present invention in mammals will vary according to the size of the animal and particularly with respect to the brain/body weight ratio. In general, a higher mg/kg dosage for a small animal such as a dog will have the same effect as a lower mg/kg dosage in an adult human. A minimum effective dosage for a compound of formula (I) will be at least about 0.1 mg/kg of body weight per day for mammals with a maximum dosage for a small mammal such as a dog, of about 100 mg/kg per day. For humans, a dosage of about 0.1 to 12 mg/kg per day will be effective, e.g., about 5 to 600 mg/day for an average man. The dosage can be given once daily or in divided doses, e.g., 2 to 4 doses daily, and such will depend on the duration and maximum level of activity of a particular compound. The dose may be conventionally formulated in an oral or parenteral dosage form by compounding about 10 to 250 mg per unit of dosage of conventional vehicle, excipient, binder, preservative, stabilizer, flavor or the like as called for by accepted pharmaceutical practice, e.g., as described in U.S. Pat. No. 3,755,340.

Among the tests conducted to demonstrate the anxiolytic activity of the present compounds was the Shock-Induced Suppression of Drinking (Rats) (SSD) Test, described in Pharmacology Biochemistry and Behavior, Vol. 12, pages 819-821 (1980) which was carried out as follows:

Male rats in the weight range of 200 to 220 grams are deprived of water for 48 hours and deprived of food for 24 hours before testing. Normally, the rats are orally intubated (5 ml/kg) with the test compound (based on mg/kg body weight). The vehicle control group of rats is also intubated by mouth. A positive control group of rats is also orally administered a control dose of 18 mg/kg of chlordiazepoxide. Random selection of the rats is utilized in dosing. The rats are returned to the cage for one hour. Sixty minutes after drug administration, the rat is quietly removed from its cage and the hind feet wiped with Signa electrode gel made by Parker Laboratories of Orange, N.J. When intraperitoneal (i.p.) administration was used, the protocol was identical except that the drugs were administered (5 ml/kg) 30 minutes prior to testing. The rat is placed on the floor in the chamber facing the licking tube. The animal is allowed 5 minutes to make 20 licking responses and receive the first shock (0.5 mA). If this response does not occur, the animal is removed and eliminated from the study. If 20 licking responses are made, the animal is permitted an additional 3 minutes during which time each 20th lick is paired with a 0.5 mA shock. This period is automatically started, counted and terminated. The number of licks and shocks are recorded. The activity of the compound tested is evaluated by comparing the mean shocks of the group dosed with the test compound to both the mean shocks of the vehicle and positive control groups via a Students' t-test. In general, an increase in the number of shocks received compared to the control is indicative of the anti-conflict or anti-anxiety activity of the compound.

In the SSD test, the compound of the invention of formula (II) wherein $R^1$ is n-pentyl; $R^3$ is hydrogen; $R^4$ is hydrogen: D is $NCH_2CH_2CH_3$ or $NCH_2CH=CH_2$; and $R^7$ and $R^8$ are hydrogen showed activity as indicated by a significant (P (probability) is less than 0.05, Students' t-test) increase in the number of shocks taken.

A second test for anxiolytic activity conducted on compounds of the invention was the [$^3H$]flunitrazepam binding test described in the European Journal of Pharmacology, Vol. 78, pages 315-322 (1982) by B. A. Meiners and A. I. Salama, which test is conducted as follows:

A lysed mitochondrial-synaptosomal ($P_2$) fraction was prepared from the cerebral cortex of male Sprague-Dawley rats weighing 150-250 g, according to the method of Braestrup and Squires in the Proceedings of the National Academy of Science U.S.A., Vol. 74, page 3805 (1977). The fraction was then washed twice by centrifugation in 50 mM Tris-HCl pH 7.4 buffer.

Specific flunitrazepam binding was measured by a filtration assay similar to that of Wastek et al. in the European Journal of Pharmacology, Vol. 50, page 445 (1978). The 2 ml assays contained 0.2 nM [$^3H$]flunitrazepam (84 Ci/mmol) and membranes equivalent to 10 mg fresh weight (0.2 mg protein) in 50 mM Tris-HCl pH 7.4 buffer. Drugs were added in 10 μl 95% ethanol which was also added to the control. Non-specific binding was 5 determined in the presence of 2.5 μM clonazepam or 0.5 μM flunitrazepam. The samples were allowed to equilibrate for 90 min. at 0° C. before being filtered and rinsed. Typical assays were done in triplicate, each gave approximately 4000 cpm total of which 150 cpm were due to non-specific binding. Determinations of affinity and maximum binding were made by adding different amounts of non-radioactive flunitrazepam to 0.2 nM [$^3$H]flunitrazepam.

Anxiolytic activity is indicated in the flunitrazepam binding test by a displacement of the flunitrazepam such as is exhibited by benzodiazepines or by enchancement of the binding such as is shown by cartazolate and tracazolate. In the flunitrazepam binding test, the compound of the invention of formula (II) wherein $R^1$ is n-pentyl; $R^3$, $R^4$, $R^7$ and $R^8$ are hydrogen; and D is $NCH_2CH_2CH_3$, and the corresponding compound wherein D is $NCH_2CH=CH_2$, showed activity as displacers of flunitrazepam binding.

None of the compounds of the formula (I) which have been tested in the above-mentioned tests has exhibited any signs of toxicity. Furthermore, the compound of the formula (I) described in Example 5 below has an approximate oral $LD_{50}$ in the rat of over 800 mg/kg, and when the same compound was administered orally to monkeys at 100 mg/kg, it caused no deaths.

Novel intermediates of the invention include those of the formulae (VII), (VIIII), (XIIA), (XVI) and (XVII).

Synthesis of compounds of the invention is demonstrated by the following Examples, degrees being in Centigrade (C) and the following abbreviations being used: mg (milligrams), kg (kilograms), g (grams), psi (pounds per square inch pressure), mM (millimole), ml (milliliters), tlc (thin layer chromatography), mm (millimeters), bp (boiling point), NMR (nuclear magnetic resonance), MS (mass spectrum), m/e (mass to charge ratio); DMF (dimethylformamide); THF (tetrahydrofuran); and mp (melting point). Conventional chemical abbreviations for the elements, e.g., C, H, N, and O, are also used.

EXAMPLE 1 a. 5-Amino-1-n-pentylpyrazole (Formula (III), $R^1$=n-pentyl and $R^3$=H)

To a stirred solution of 40.27 g (0.473 mole) of 2-cyanoethylhydrazine in 348 ml of toluene was added dropwise a solution of 42.8 g (0.497 mole) of valeraldehyde in 87 ml of toluene whereupon a slight exothermic reaction occurred. After stirring 3 hours at room temperature, the reaction mixture was concentrated to give 80.50 g of the intermediate hydrazone as an amber oil.

This oil was then added to a solution of sodium butoxide, prepared by dissolving 2.0 g (87 mg atoms) of sodium in 435 ml of butanol, and heated at reflux for 5 hours. The resulting cooled solution was concentrated to leave 89.7 g of a dark viscous oil which was distilled to give 31.68 g of 5-amino-1-n-pentylpyrazole as a light yellow oil, bp=106°-112° at 0.35-0.4 mm of Hg; tlc, $R_f$=0.3, silica gel, ethyl acetate:hexane (1:1); MS, m/e=153.

b.
4-Hydroxy-6-methyl-1-n-pentyl-1H-pyrazolo[3,4-b]pyridine-5-carboxylic acid ethyl ester (Formula (V), $R^1$=n-pentyl, $R^3$=H, R=ethyl, $R^7$=H, $R^8$=H)

To 52 g of stirred polyphosphoric acid was added 12.02 g (78.4 mM) of the pyrazole produced in Example 1a. and 15.86 g (78.4 mM) of diethylacetylmalonate. The resulting mixture was then stirred at 120° for 3 hours, allowed to cool and then diluted with water with vigorous stirring. The resulting mixture was extracted with four portions of diethylether which were combined, dried with MgSO$_4$, filtered and concentrated to leave 18.25 g of the product ester as an amber oil which slowly crystallized. Recrystallization from hexane gave the product as a white solid; mp=49°-51° C.; tlc, $R_f$=0.4, silica gel, diethylether:hexane (1:1); MS, m/e=291.

Elemental Analysis: Calculated for $C_{15}H_{21}N_3O_3$: C, 61.84; H, 7.27; N, 14.42; Found: C, 61.64; H, 7.12; N, 14.56.

The amber oil crude product may be purified by dissolving it in ethyl acetate and adding hydrochloric acid to obtain salt crystals mp=141°-143° C. or sulfuric acid to obtain salt crystals mp=151°-153° C.

c.
4-Chloro-6-methyl-1-n-pentyl-1H-pyrazolo[3,4-b]pyridine-5-carboxylic acid ethyl ester (Formula (VI), $R^1$=n-pentyl, $R^3$=H, X=Cl, R=ethyl, $R^7$=H, $R^8$=H)

A solution of 1.05 g (3.60 mM) of the product of Example 1b. and 4.5 ml (49 mM) of phosphorus oxychloride was refluxed for 3.2 hours and then concentrated to remove the excess phosphorus oxychloride. The residue was diluted with water and the resulting mixture extracted with diethylether, dried with MgSO$_4$, filtered and concentrated to leave 0.83 g of the product as an amber oil; tlc, $R_f$=0.8, silica gel, diethylether:hexane (1:1); MS, m/e=309, 311.

d.
4-Chloro-6-methyl-1-n-pentyl-1H-pyrazolo[3,4-b]pyridine-5-carboxylic acid ethyl ester 7-oxide (Formula (VII), $R^1$=n-pentyl, $R^3$=H, X=Cl, R=ethyl, $R^7$=H, $R^8$=H)

A solution of 16.0 g (51.6 mM) of the product of Example 1c. and 26.74 g (131.7 mM) of 85% m-chloroperoxybenzoic acid in 260 ml of glacial acetic acid was stirred at 65° for 3 hours. The solution was then concentrated and the solid residue was triturated with 300 ml of cold hexane and filtered to separate the solids. The filtrate was washed with saturated aqueous sodium carbonate and water and then dried with MgSO$_4$, filtered and concentrated to leave 16.53 g of a pale yellow oil, which was shown by silica gel tlc in the solvent system of hexane:diethylether (1:1) to consist of the starting pyrazolopyridine ($R_f$=0.8) and the desired N-oxide ($R_f$=0.4). The oil was chromatographed on a silica gel column using the solvent system of hexane:diethylether (2:1) as the eluent to separat.e 5.58 g of the starting pyrazolopyridine and 7.93 g of title 7-oxide compound as a pale yellow oil: MS, m/e=325, 327.

e.
6-Acetoxymethyl-4-chloro-1-n-pentyl-1H-pyrazolo[3,4-b]pyridine-5-carboxylic acid ethyl ester (Formula (VIII), $R^1$=n-pentyl, $R^3$=H, X=Cl, R=ethyl, $R^{11}$=methyl, $R^7$=H, $R^8$=H)

A solution of 5.0 g (15.3 mM) of the 7-oxide produced in Example 1d. in 30 ml of acetic anhydride and 30 mls of glacial acetic acid was refluxed for 20 minutes and then concentrated to leave a pale yellow oil which was taken up in diethylether and stirred over aqueous sodium bicarbonate for 20 minutes. The ether layer was separated, dried over MgSO$_4$, filtered and concentrated to leave 5.53 g of the title 6-acetoxymethyl compound as a yellow oil: tlc, $R_f$=0.8, silica gel, diethylether:hexane (1:1); MS, m/e=367, 369.

f.
4-Amino-1,7-dihydro-1-n-pentyl-5H-furo[3,4-b]pyrazolo[4,3-e]pyridin-5-one (Formula (I), $R^1$=n-pentyl, $R^3$=H, $R^4$=H, D=O, n=1, $R^7$=H, $R^8$=H)

A solution of 3.90 g (10.6 mM) of the 6-acetoxymethyl compound produced in Example 1e. in 25 ml of ethanol saturated with ammonia was placed in a stainless steel pressure vessel and heated at 115°–120° C. for 12 hours. The resulting cooled reaction mixture was poured into 150 ml of water and the resulting precipitate collected and air-dried. Recrystallization of this solid from toluene gave 2.28 g of the desired title lactone as tan needles, mp=187°–188.5°; tlc, $R_f$=0.7, silica gel, methanol:chloroform (7:93); MS, m/e=260.

Elemental Analysis: Calculated for $C_{13}H_{16}N_4O_2$: C, 59.98; H, 6.20; N, 21.53; Found: C, 60.20; H, 6.19; N, 21.57.

EXAMPLE 2

4-n-Butylamino-1,7-dihydro-1-n-pentyl-5H-furo[3,4-b]pyrazolo[4,3-e]pyridin-5-one (Formula (I), $R^1$=n-pentyl, $R^3$=H, $R^4$=n-butyl, D=O, n=1, $R^7$=H, $R^8$=H)

A solution of 1.53 g (4.16 mM) of the acetoxymethyl compound prepared in Example 1e. in 10 ml of n-butylamine was stirred at room temperature for 20 hours and then poured into water. The resulting precipitate was collected and air-dried to give 1.33 g of a tan solid which was chromatographed over silica gel, using 4% methanol in methylene chloride as the eluent. The fractions containing the desired lactone were combined and concentrated to leave 1.03 g of a tan solid. Recrystallization of this solid from ethyl acetate gave 0.83 g of the desired lactone as pale yellow crystals, mp=127.5°–128.5°; tlc, $R_f$=0.25, silica gel, acetone:hexane (1:9); MS, m/e=316.

Elemental Analysis: Calculated for $C_{17}H_{24}N_4O_2$: C, 64.53; H, 7.65; N, 17.71; Found: C, 64.37; H, 7.57; N, 17.78.

EXAMPLE 3 a. 5-Amino-1-n-butylpyrazole (Formula (III), $R^1$=n-butyl)

The title compound was prepared according to the procedure of Example 1a. using n-butyraldehyde in the place of valeraldehyde. The pyrazole product was obtained as a clear oil; bp=96°–98° at 0.55 to 0.65 mm of Hg; tlc, $R_f$=0.3, silica gel, diethylether; MS, m/e=139.

b.
1-n-Butyl-4-hydroxy-6-methyl-1H-pyrazolo[3,4-b]pyridine-5-carboxylic acid ethyl ester (Formula (V), $R^1$=n-butyl, $R^3$=H, R=ethyl, $R^7$=, $R^8$=H)

The title compound was prepared according to the procedure of Example 1b. using the product of Example 3a. in the place of the product of Example 1a. The title compound was obtained as an amber oil; tlc, $R_f$=0.7; silica gel, methanol:chloroform:triethylamine (3:97:1); MS, m/e=277.

c.
1-n-Butyl-4-chloro-6-methyl-1H-pyrazolo[3,4-b]pyridine-5-carboxylic acid ethyl ester (Formula (VI), $R^1$=n-butyl, $R^3$=H, X=Cl, R=ethyl, $R^7$=H, $R^8$=H)

The title compound was prepared according to the procedure of Example 1c. utilizing the product produced in Example 3b. in the place of that produced in Example 1b; tlc, $R_f$=0.7, silica gel, diethylether:hexane (1:1); MS, m/e=295, 297.

d.
1-n-Butyl-4-chloro-6-methyl-7-oxide-1H-pyrazolo[3,4-b]pyridine-5-carboxylic acid ethyl ester (Formula (VII), $R^1$=n-butyl, $R^3$=H, X=Cl, R=ethyl, $R^7$=H, $R^8$=H)

The title compound was prepared according to the procedure of Example 1d. utilizing the product of Example 3c. in the place of the product of Example 1c. The title compound was obtained as a light yellow solid; tlc, $R_f$=0.3, silica gel, diethylether:hexane (1:1); MS, m/e=311, 313.

e.
6-Acetoxymethyl-1-n-butyl-4-chloro-1H-pyrazolo[3,4-b]pyridine-5-carboxylic acid ethyl ester (Formula (VIII), $R^1$=n-butyl, $R^3$=H, X=Cl, R=ethyl, $R^{11}$=methyl, $R^7$=H, $R^8$=H)

The title compound was prepared according to the procedure of Example 1e. utilizing the product of Example 3d. in the place of the product produced in Example 1d. The title compound was obtained as a light amber oil; tlc, $R_f$=0.6, silica gel, diethylether:hexane (1:1), MS, m/e=353, 355.

f.
4-Amino-1-n-butyl-1,7-dihydro-5H-furo[3,4-b]pyrazolo[4,3-e]pyridin-5-one (Formula (I), $R^1$=n-butyl, $R^3$=H, $R^4$=H, D=O, n=1, $R^7$=H, $R^8$=H)

The title compound was prepared according to the procedure of Example 1f. utilizing the product of Example 3e. in the place of the product produced in Example 1e. The title compound was obtained as white crystals, mp=212°–213°; tlc, $R_f$=0.5, silica gel, chloroform:methanol (93:7); MS, m/e=246.

Elemental Analysis: Calculated for $C_{12}H_{14}N_4O_2$: C, 58.53; H, 5.73; N, 22.75; Found: C, 58.71; H, 5.74; N, 22.96.

EXAMPLE 4

6-Allyl-4-amino-6,7-dihydro-1-n-pentylpyrazolo[3,4-b]pyrrolo[3,4-e]pyridin-5(1H)-one (Formula (I), $R^1$=n-pentyl, $R^3$=H, $R^4$=H, D=$NR^6$, $R^6$=$CH_2CH$=$CH_2$, n=1, $R^7$=H, $R^8$=H)

A solution of 0.32 g (1.2 mM) of the lactone prepared in Example 1f. in 7 ml of 3-aminoprop-1-ene was heated in a sealed stainless steel pressure vessel at 185°–200° for 12 hours and then concentrated to leave a solid. The solid was chromatographed over silica gel using the solvent system of ethyl acetate:hexane (3:2) as the eluent to give 0.29 g of the title lactam as a white solid. Recrystallization from toluene/hexane gave 0.25 g of the allyl lactam as white crystals, mp=136.5°–137.5°; tlc, $R_f$=0.3, silica gel, ethyl acetate:hexane (2:1); MS, m/e=299.

Elemental Analysis: Calculated for $C_{16}H_{21}N_5O$: C, 64.19; H, 7.07; N, 23.40; Found: C, 64.26; H, 7.20; N, 23.16.

EXAMPLE 5

4-Amino-6,7-dihydro-1-n-pentyl-6-n-propyl-
pyrazolo[3,4-b]pyrrolo[3,4-e]pyridin-5(1H)-one
(Formula (I), $R^1$=n-pentyl, $R^3$=H, $R^4$=H, D=$NR^6$,
$R^6$=n-propyl, n=1, $R^7$=H, $R^8$=H)

The procedure of Example 4 was followed with the exception of using 0.84 g (3.2 mM) of the lactone prepared in Example 1f. and 7 ml of n-propylamine as the starting materials. The solution was heated in a sealed stainless steel pressure vessel at 185°–200° for 12 hours and then concentrated to leave 1.05 g of a tan solid. The solid was chromatographed over silica gel using the solvent system of ethyl acetate:hexane (3:2) as the eluent to give 0.78 g of the desired lactam as a white solid. Recrystallization of this solid from toluene/hexane gave 0.75 g of the lactam as white crystals, mp=146°–146.5°; tlc, $R_f$=0.3, silica gel, ethyl acetate:hexane (2:1); MS, m/e=301.

Elemental Analysis: Calculated for $C_{16}H_{23}N_5O$: C, 63.76; H, 7.69; N, 23.24; Found: C, 63.77; H, 7.76; N, 23.22.

The hydrochloride salt of the product of Example 5 was prepared, mp=209°–218° C.

EXAMPLE 6

4-Amino-6-n-butyl-6,7-dihydro-1-n-pentylpyrazolo[3,4-
b]pyrrolo[3,4-e]pyridin-5(1H)-one (Formula (I),
$R^1$=n-pentyl, $R^3$=H, $R^4$=H, D=$NR^6$, $R^6$=n-butyl,
n=1, $R^7$=H, $R^8$=H)

The title compound was prepared according to the procedure of Examples 4 and 5 utilizing n-butylamine in the place of 3-aminoprop-1-ene or n-propylamine. The product was obtained as a white solid: mp=116.8°–118° C.; tlc, $R_f$=0.4, silica gel, ethyl acetate; MS, m/e=315.

Elemental Analysis: Calculated for $C_{17}H_{25}N_5O$: C, 64.73; H, 7.99; N, 22.20; Found: C, 64.67; H, 8.13; N, 22.23.

EXAMPLE 7

4-Amino-6,7-dihydro-6-methyl-1-n-pentylpyrazolo[3,4-
b]pyrrolo[3,4-e]pyridin-5(1H)-one (Formula(I),
$R^1$=n-pentyl, $R^3$=H, $R^4$=H, D=$NR^6$, $R^6$=methyl,
n=1, $R^7$=H, $R^8$=H)

A solution of 1.39 g (5.34 mM) of the lactone prepared in Example 1f. in 25 ml of methylamine was heated in a stainless steel pressure vessel at 170°–200° C. for 12 hours and then concentrated to leave a tacky solid. The solid was chromatographed over silica gel using the solvent system of hexane:acetone (3:2) as the eluent to give 0.73 g of a white solid. The solid was recrystallized from toluene to give 0.40 g of the title lactam as white crystals, mp=163.8°–169.5° C.; tlc, $R_f$=0.3, silica gel, hexane:acetone (3:2); MS, m/e=273.

Elemental Analysis: Calculated for $C_{14}H_{19}N_5O$: C, 61.52; H, 7.01; N, 25.62; Found: C, 61.70; H, 7.11; N, 25.91.

EXAMPLE 8

4-Amino-6,7-dihydro-6-ethyl-1-n-pentylpyrazolo[3,4-
b]pyrrolo[3,4-e]pyridin-5(1H)-one (Formula (I),
$R^1$=n-pentyl, $R^3$=H, $R^4$=H, D=$NR^6$, $R^6$=ethyl,
n=1, $R^7$=H, $R^8$=H)

The procedure of Example 7 was followed with the exception of using 1.26 g of the lactone prepared in Example 1f and 12 ml of ethylamine (condensed by dry ice condenser) as the starting materials. The solution was heated in a sealed stainless steel pressure vessel at 170°–200° C. for 12 hours and then concentrated to leave a white solid. The solid was chromatographed over silica gel using the solvent system of ethyl acetate:hexane (5:1) as the eluent to yield 1.16 g of a white solid. The solid was recrystallized from toluene/hexane to give 1.15 g of the title lactam as a white solid, mp=157.3°–157.9° C.; tlc, $R_f$=0.3–0.4, silica gel, ethyl acetate; MS, m/e=287.

Elemental Analysis: Calculated for $C_{15}H_{21}N_5O$: C, 62.69; H, 7.37; N, 24.37; Found: C, 62.62; H, 7.22; N, 24.71.

EXAMPLE 9

4-Amino-6,7-dihydro-1-n-pentyl-6-isopropyl-
pyrazolo[3,4-b]pyrrolo[3,4-e]pyridin-5(1H)-one
(Formula (I), $R^1$=n-pentyl, $R^3$=H, $R^4$=H, D=$NR^6$,
$R^6$=i-propyl, n=1, $R^7$=H, $R^8$=H)

The procedure of Example 7 was followed with the exception of using 1.24 g of the lactone prepared in Example 1f and 11 ml of isopropylamine as the starting materials. The solution was heated in a stainless steel pressure vessel at 188°–192° C. for 12 hours and then concentrated to yield 1.76 g of an amber solid (theoretical=1.43 g). The solid was chromatographed on silica gel using the solvent system of ethyl acetate:hexane (3:2) as the eluent to yield 0.96 g of a white solid. The solid was recrystallized from toluene/hexane to give the title lactam as 0.84 g of a white crystalline solid, mp=151.5°–155.0° C.; tlc, $R_f$=0.3, silica gel, ethyl acetate:hexane (3:2); MS, m/e=301.

Elemental Analysis: Calculated for $C_{16}H_{23}N_5O$: C, 63.76; H, 7.69; N, 23.24; Found: C, 63.75; H, 7.59; N, 23.40.

EXAMPLE 10

4-Amino-6-isobutyl-6,7-dihydro-1-n-pentyl-
pyrazolo[3,4-b]pyrrolo[3,4-e]pyridin-5(1H)-one
(Formula (I), $R^1$=n-pentyl, $R^3$=H, $R^4$=H, D=$NR^6$,
$R^6$=isobutyl, n=1, $R^7$=H, $R^8$=H)

The procedure of Example 7 was followed with the exception of using 1.21 g of the lactone prepared in Example 1f. and 12 ml of isobutylamine as the starting materials. The solution was heated at 170°–200° C. for 24 hours and then concentrated to yield 1.58 g of a tan solid (theoretical=1.47 g). The solid was recrystallized from toluene/hexane to yield 1.16 g of an off-white solid. The solid was chromatographed on silica gel using the solvent system of ethyl acetate/hexane (5:4) as the eluent to yield 0.86 of a white solid which was recrystallized from toluene/hexane to give 0.80 g of the title lactam as a white solid, mp=142.0°–144.1° C.; tlc, $R_f$=0.3, silica gel, ethyl acetate:hexane (1:1); MS, m/e=315.

Elemental Analysis: Calculated for $C_{17}H_{25}N_5O$: C, 64.73; H, 7.99; N, 22.20; Found: C, 64.56; H, 7.92; N, 22.50.

EXAMPLE 11

4-Amino-6-benzyl-6,7-dihydro-1-n-pentylpyrazolo[3,4-
b]pyrrolo[3,4-e]pyridin-5(1H)-one (Formula (I),
$R^1$=n-pentyl, $R^3$=H, $R^4$=H, D=$NR^6$, $R^6$=benzyl,
n=1, $R^7$=H, $R^8$=H)

The title compound was prepared according to the procedure of Example 7 utilizing 1.14 g of the lactone prepared in Example 1f. and 12 ml of benzylamine. The product was obtained as a light-tan solid (2.16 g, theoretical=1.53 g) after Kugelrohr distillation to remove the excess benzylamine. The solid was recrystallized from toluene/hexane to yield 1.26 g of a white solid, mp=139.0°-141.5° C.; tlc, $R_f$=0.3, silica gel, ethyl acetate:hexane (1:1); MS, m/e=349.

Elemental Analysis: Calculated for $C_{20}H_{23}N_5O$: C, 68.74; H, 6.63; N, 20.04; Found: C, 68.56; H, 6.73; N, 19.85.

EXAMPLE 12

4-Amino-6,7-dihydro-1-n-pentyl-6-(2,2,2-trifluoroethyl)pyrazolo[3,4-b]pyrrolo[3,4-e]pyridin-5(1H)-one (Formula (I), $R^1$=n-pentyl, $R^3$=H, $R^4$=H, D=NR$^6$, $R^6$=2,2,2-trifluoroethyl, n=1, $R^7$=H, $R^8$=H)

A solution of 1.94 g of the lactone prepared in Example 1f in 19 ml of 2,2,2-trifluoroethylamine was heated in a stainless steel bomb pressure vessel at 220°-225° C. for 90 hours and then concentrated to give a thick residue. The residue was suspended in toluene and recollected to give 2.06 g of a light-tan solid (theoretical=2.54 g). The solid was recrystallized from toluene to give the title lactam as an off-white solid, mp=144.8°-146.3° C.; tlc, $R_f$=0.7, silica gel, ethyl acetate; MS, m/e=341.

Elemental Analysis: Calculated for $C_{15}H_{18}F_3N_5O$: C, 52.78; H, 5.32; N, 20.52; Found: C, 52.95; H, 5.51; N, 20.39.

EXAMPLE 13

4Amino-6,7-dyhydro-1-n-pentyl-6-phenylpyrazolo[3,4-b]pyrrolo[3,4-e]pyridin-5(1H)-one (Formula (I), $R^1$=n-pentyl, $R^3$=H, $R^4$=H, D=NR$^6$, $R^6$=phenyl, n=1, $R^7$=H, $R^8$=H)

A solution of 2.27 g of the lactone prepared in Example 1f in 21 ml of distilled aniline was heated in a stainless steel pressure vessel at 200°-210° C. for 15 hours and then concentrated (Kugelrohr, 35°-45° C., high vacuum) to give a dark, amber semi-solid (3.96 g, theoretical=2.93 g). The semi-solid was chromatographed on silica gel using the solvent system hexane:ethyl acetate (3:2) as the eluent to give 1.79 g of a tan solid which consisted of two components as indicated by tlc. The tan solid was chromatographed by high pressure liquid chromatography on silica gel using ethyl acetate:chloroform (4:1) as the eluent to give 0.48 g of a light-tan solid. The solid was recrystallized from toluene to yield 0.45 g of a light-tan solid, mp=201°-203° C.; tlc, $R_f$=0.4, silica gel, ethyl acetate:hexane (1:1); MS, m/e=335.

Elemental Analysis: Calculated for $C_{19}H_{21}N_5O$: C, 68.04; H, 6.31; N, 20.88; Found: C, 68.15; H, 6.52; N, 21.24.

EXAMPLE 14

4-Amino-6-cyclopropylmethyl-6,7-dihydro-1-n-pentylpyrazolo[3,4-b]pyrrolo[3,4-e]pyridin-5(1H)-one (Formula (I), $R^1$=n-pentyl, $R^3$=H, $R^4$=H, D=NR$^6$, $R^6$=cyclopropylmethyl, n=1, $R^7$=H, $R^8$=H)

A suspension of 1.37 g of the lactone prepared in Example 1f. and 5.7 g of cyclopropylmethylamine hydrochloride in 23 ml of triethylamine was heated in a stainless steel pressure vessel at 170°-200° C. for 12 hours and then concentrated. The residue was suspended in water and extracts were washed with water, dried over MgSO$_4$, filtered, and concentrated to give 1.62 g (theoretical=1.65 g) of a light-tan solid. The solid was chromatographed on silica gel using the solvent system ethyl acetate:hexane (2:1) to give 1.27 g of a light-pink solid. The solid was recrystallized from toluene/hexane to give the title lactam as 1.17 g of a white solid, mp=125.5°-126.3° C.; tlc, $R_f$=0.4, silica gel, ethyl acetate: MS, m/e=313.

Elemental Analysis: Calculated for $C_{17}H_{23}N_5O$: C, 65.15; H, 7.40; N, 22.35; Found: C, 65.06; H, 7.30; N, 22.58.

EXAMPLE 15

4-Amino-6,7-dihydro-1-n-pentylpyrazolo[3,4-b]pyrrolo[3,4-e]pyridin-5(1H)-one (Formula (I), $R^1$=n-pentyl, $R^3$=H, $R^4$=H, D=NR$^6$, $R^6$=H, n=1, $R^7$=H, $R^8$=H)

A suspension of 3.00 g of the lactone prepared in Example 1f. and approximately 45 ml of liquid ammonia which had been condensed in a dry ice trap was heated in a stainless steel pressure vessel at 160°-170° C. for 90 hours and then concentrated to give 2.90 g of a tan solid (theoretical=2.98 g). The tan solid and 0.44 g of similarly prepared product were combined and recrystallized from DMF to give 2.63 g of the title lactam as yellow crystals, mp=284°-290° C.; tlc, $R_f$=0.3, silica gel, chloroform:methanol (93:7); MS, m/e=259.

Elemental Analysis: Calculated for $C_{13}H_{17}N_5O$: C, 60.21; H, 6.61; N, 27.01; Found: C, 59.93; H, 6.54; N, 27.16.

EXAMPLE 16

4-n-Butylamino-6,7-dihydro-1-n-pentyl-6-n-propylpyrazolo[3,4-b]pyrrolo[3,4-e]pyridin-5(1H)-one (Formula (I), $R^1$=n-pentyl, $R^3$=H, $R^4$=n-butyl, D=NR$^6$, $R^6$=n-propyl, n=1, $R^7$=H, $R^8$=H)

The propyl lactam amine (2.27 g) prepared in Example 5 was added in several portions to a stirred suspension of 1.1 equivalents of sodium hydride (from 0.40 g of 50% NaH in nujol, hexane washed) in 78 ml of DMF at room temperature. A clear solution formed after 0.5 hours. 1-iodobutane (0.90 ml, 1.1 equivalent) was added to this solution in a single portion. After 5 hours at room temperature, the DMF was evaporated and the mixture was poured into H$_2$O, then extracted with ether. The ether extracts were washed with water, dried over MgSO$_4$, and concentrated to give 2.77 g (theoretical=2.69 g) of a clear, yellow oil. The oil was chromatographed on silica gel using the solvent system diethyl ether:hexane (3:2) as the eluent to give 2.42 g of a light-yellow oil. The oil was crystallized from hexane by cooling in a dry ice/acetone bath to give 2.03 g of the title compound as a white solid, mp=44°-51° C.; tlc, $R_f$=0.6, silica gel, ethyl acetate/hexane (1:1); MS, m/e=357.

Elemental Analysis: Calculated for $C_{20}H_{31}N_5O$: C, 67.19; H, 8.74; N, 19.59; Found: C, 67.04; H, 8.64; N, 19.51.

EXAMPLE 17

6,7-Dihydro-1-n-pentyl-4-n-propylamino-6-n-propylpyrazolo[3,4-b]pyrrolo[3,4-e]pyridin-5(1H)-one (Formula (I), $R^1$=n-pentyl, $R^3$=H, $R^4$=n-propyl, D=NR$^6$, $R^6$=n-propyl, n=1, $R^7$=H, $R^8$=H)

The title compound was prepared according to Example 16 utilizing 1.18 g of the lactam prepared in Example 5, 0.21 g of 50% sodium hydride in nujol, and 0.40 ml of 1-iodopropane in 41 ml of DMF. The crude product was obtained as 1.26 g (theoretical=1.35 g) of a light-yellow oil. The oil was chromatographed on silica gel using the solvent system diethyl ether:hexane (3:2) to give 1.18 g of a colorless oil. The oil was crystallized from cold hexane (dry ice/acetone bath) to give 0.93 g of the title lactam as a white solid, mp=36°-47° C.; tlc, $R_f$=0.5, silica gel, ethyl acetate:hexane (1:1); MS, m/e=343.

Elemental Analysis: Calculated for $C_{19}H_{29}N_5O$: C, 66.44; H, 8.51; N, 20.39; Found: C, 66.18; H, 8.49; N, 20.15.

EXAMPLE 18

4-Acetylamino-6,7-dihydro-1-n-pentyl-6-n-propyl-pyrazolo[3,4-b]pyrrolo[3,4-e]pyridin-5(1H)-one (Formula (I), $R^1$=n-pentyl, $R^3$=H, $R^4$=acetyl, D=$NR^6$, $R^6$=n-propyl, n=1, $R^7$=H, $R^8$=H)

The propyl lactam amine prepared in Example 5 (0.96 g) was suspended in 16 ml of dry toluene. To this was added 0.19 g, 0.5 equivalent, of p-dimethylaminopyridine followed by 3.26 g (10 equivalent) of acetic anhydride. The mixture was refluxed for 4 hours. Another portion (0.19 g, 0.5 equivalent) of p-dimethylaminopyridine was added and the mixture refluxed for an additional 1.5 hours. The mixture was poured into 300 ml of water, treated with sodium bicarbonate, and extracted with ether. The ether extracts were dried over $MgSO_4$, and concentrated to give 1.23 g (theoretical=1.10 g) of an amber oil. The oil was crystallized from toluene:hexane (dry ice/acetone bath) to give the title lactam as 0.80 g of an off-white solid, mp=67.9°-70.0° C., tlc, $R_f$=0.7, silica gel, diethyl ether: MS, m/e=343.

Elemental Analysis: Calculated for $C_{18}H_{25}N_5O_2$: C, 62.95; H, 7.34; N, 20.39; Found: C, 63.10; H, 7.20; N, 20.86.

EXAMPLE 19 a. 5-Amino-1-(3-methylbutyl)pyrazole (Formula (III), $R^1$=$CH_2$—$CH_2CH(CH_3)_2$, $R^3$=H)

The procedure of Example 1a was followed using 26.14 g (303.5 mM) of isovaleraldehyde in 53 ml of toluene and 24.56 g (288.6 mM) of cyanoethylhydrazine in 202 ml of toluene to give 46.7 g of the intermediate hydrazone as an amber oil. This hydrazone was then cyclized to the aminopyrazole using the procedure of Example 1a using 1.1 g (48 mg atoms) of sodium in 265 ml of 1-butanol and extending the reflux period to 18 hours. Distillation of the crude aminopyrazole gave 20.93 g of 5-amino-1-(3-methylbutyl)pyrazole as a light yellow oil, bp=98°-101° C. at 0.3-0.35 mm of Hg; tlc, $R_f$=0.5, silica gel, diethylether: MS, m/e=153.

The pyrazole product of Example 19a. was then carried through the procedures of Example 1b. and 1c. to yield 4-chloro-6-methyl-1-(3-methyl-n-butyl)-1H-pyrazolo[3,4-b]pyridine-5-carboxylic acid ethyl ester.

b.

4-Chloro-6-methyl-1-(3-methyl-n-butyl)-7-oxide-1H-pyrazolo[3,4-b]pyridine-5-carboxylic acid ethyl ester (Formula (VII), $R^1$=$CH_2CH_2CH(CH_3)_2$, $R^3$=H, X=Cl, R=$CH_2CH_3$, $R^7$=H, $R^8$=H)

A solution of 8.0 g (26 mM) of the 4-chloro ethyl ester compound prepared above in 25 ml of methylene chloride was added to a stirring solution of trifluoroperoxyacetic acid in methylene chloride. The temperature of the mixture must not exceed 30° C. The trifluoroperoxyacetic acid was prepared by slowly adding 0.95 ml (39 mM) 90% hydrogen peroxide to a stirred solution of 6.57 ml (46.5 mM) trifluoroacetic anhydride in 25 ml methylene chloride at 0° C., then at room temperature for a further 30 minutes. After the addition of chloro compound, the reaction was stirred at room temperature for 2 hours and subsequently poured into 300 ml $H_2O$. A solution of 4.9 g sodium sulfite in 45 ml $H_2O$ was carefully added with stirring and the mixture was checked for peroxides with peroxide paper. Solid sodium bicarbonate was added until the reaction mixture was basic. The mixture was extracted with methylene chloride then dried over magnesium sulfate, filtered and concentrated to a brown oil. The oil was chromatographed over silica gel using the solvent system of ethyl acetate:hexane (1:3) as the eluent to give 4.36 g (52%) of the desired N-oxide as an oil; tlc, $R_f$=0.3, silica gel, ethyl acetate:hexane (1:3).

c.

6-Acetoxymethyl-4-chloro-1-(3-methyl-n-butyl)-1H-pyrazolo[3,4-b]pyridine-5-carboxylic acid ethyl ester (Formula (VIII), $R^1$=$CH_2CH_2CH(CH_3)_2$, $R^3$=H, X=Cl, R=$CH_2CH_3$, $R^{11}$=$CH_3$, $R^7$=H, $R^8$=H)

The title compound was prepared by adding 27 ml acetic anhydride to a solution of 4.36 g (13.4 mM) of the N-oxide prepared in Example 19b., in 27 ml of acetic acid. The reaction mixture was heated under reflux for 20 minutes, then concentrated, treated with ether, and basified with aqueous saturated sodium bicarbonate. After drying over magnesium sulfate, filtering, and concentrating, there was obtained a yellow oil, 3.02 g (61%); tlc, $R_f$=0.5, silica gel, ethyl acetate:hexane (1:3).

d.

4-Amino-1,7-dihydro-1-(3-methyl-1-butyl)-5H-furo[3,4-b]-pyrazolo[4,3-e]pyridin-5-one (Formula (I), $R^1$=$_2CH_2CH(CH_3)_2$, $R^3$=$R^4$=H, D=O, n=1, $R^7$=H, $R^8$=H)

A solution of 3.02 g (8.21 mM) acetate prepared in Example 19c. in 16 ml of absolute ethanol saturated with ammonia was heated in a sealed stainless steel pressure vessel at 125° C. for 12 hours. The reaction mixture was poured into 125 ml $H_2O$. The lactone precipitate was filtered, washed with $H_2O$ and dried under high pressure to yield an off-white solid. Recrystallization from toluene/hexane afforded 1.16 g (54%) of the title lactone as white crystals, mp=201°-202° C.; tlc, $R_f$=0.2, silica gel, ethyl acetate:hexane (1:3).

Elemental Analysis: Calculated for $C_{13}H_{16}N_4O_2$: C, 59.99; H, 6.20; N, 21.52; Found: C, 59.84; H, 6.31; N, 21.61.

EXAMPLE 20

4-Amino-6,7-dihydro-1-(3-methyl-1-butyl)-6-n-propyl-pyrazolo[3,4-b]-pyrrolo[3,4-e]pyridin-5(1H)-one (Formula (I), $R_1$=$CH_2CH_2CH(CH_3)_2$, $R^3$=H, $R^4$=H, D=$NR^6$, $R^6$=n-propyl, n=1, $R^7$=H, $R^8$=H)

A solution of 0.66 g (2.5 mM) of the lactone prepared in Example 19d. in 5.4 ml (66 mM) n-propyl amine was heated in a sealed stainless steel pressure vessel at 185°-200° for 12 hours, then concentrated to an off-white solid. Recrystallization from toluene/hexane yielded 0.57 g (74%) of the propyl lactam as white crystals, mp=155°-156° C.; tlc, $R_f$=0.2, silica gel, ethyl acetate:hexane (1:1).

Elemental Analysis: Calculated for $C_{16}H_{23}N_5O$: C, 63.76; H, 7.69; N, 23.24; Found: C, 63.86; H, 7.82; N, 23.69.

EXAMPLE 21 a. Ethyl 3-hydroxy-4,4,4-trifluorobutyrate

A solution of 19.31 g of ethyl trifluoroacetoacetate (Fairfield Chemical) in 50 ml of ethyl acetate was hydrogenated at atmospheres on a Parr shaker over (0.5 g) $PtO_2$ as a catalyst. The volatiles were removed and the residue distilled under high vacuum to afford 14.75 g (76%) of the title compound as a low melting solid. bp=47°–49° C. at 0.1 mm of Hg, mp (uncorrected)=-about 25° C.

b. Ethyl 4,4,4-trifluorobutenoate

To a stirring solution of 22.0 g (118 mM) of the hydroxyester prepared in Example 21a. and 18.4 ml (130 mM) triethylamine in 100 ml ether at 0° C. was added 10.1 ml (130 mM) of methanesulfonylchloride. The reaction was stirred one hour at 0° C., then diluted with an equal volume of pentane and filtered through celite. The solvents were removed at room temperature: no heat was applied. The remaining oil was dissolved in ether and cooled to 0° C. With mechanical stirring, 21.2 ml (142 mM) of 1,8-diazabi-cyclo[5.4.0]undec-7-ene were added. The reaction was warmed to room temperature and stirred 3 hours. The yellow residue was dissolved by addition of 1% aqueous HCl and the solution extracted with ether. The organic phase was washed with 10% HCl, $CuSO_4$, and saturated sodium chloride, then dried over magnesium sulfate and filtered. The volatiles were removed. The title ester was distilled to yield 15.8 g (79.7%) of colorless liquid, bp=115°–120° C.

c. 4,4,4-Trifluorobutyric acid

A solution of 20.6 g (123 mM) unsaturated ester prepared in Example 21b. in 10 ml absolute ethanol was added to a stirring solution of 2.53 g (66.9 mM) sodium borohydride in 250 ml of absolute ethanol at 0° C. The mixture was kept at room temperature for 1.5 hours. Sodium hydroxide, 12.3 g (308 mM), in 20 ml $H_2O$ was added and the mixture heated at 40° C. for 1 hour. The reaction mixture was concentrated, taken up in $H_2O$, washed with ether, followed by saturated sodium chloride, then brought to a pH of 1 with 10% HCl aqueous solution, and extracted into ether. The ether layer was washed with saturated sodium chloride, dried over magnesium sulfate and filtered. The volatiles were removed followed by distillation under high vacuum to give 14.1 g (82%) of a low melting solid, bp=45° C. at 0.10 mm of Hg; mp approximately 25° C.

d. 3,3,3-Trifluoro-n-propylamine

The acid prepared in Example 21c., 5.0 g (35 mM), and 7.6 g (35 mM) of diphenylphosphoryl azide were added to a stirring solution of 5.2 ml (37 mM) of triethylamine in 100 ml of t-butanol. The reaction was heated under reflux for 14 hours, and the volatiles then removed by distillation. Ether was added and the organics were washed with 5% citric acid, 50% brine, saturated sodium bicarbonate, and saturated sodium chloride, then dried over magnesium sulfate, and filtered. The solvents were evaporated and the remaining oil was treated with 20 ml of ethereal HCl, stirred 2 hours, then concentrated to yield off-white crystals. The desired amine was distilled from dodecylamine giving 1.8 g (46%) of a colorless liquid, bp=65° C.

e. 4-Amino-6,7-dihydro-1-n-pentyl-6-(3,3,3-trifluoro-n-propyl)pyrazolo[3,4-b]pyrrolo[3,4-e]pyridin-5(1H)-one (Formula (I), $R^1$=n-pentyl, $R^3$=H, $R^4$=H, D=$NR^6$, $R^6$=$CH_2CH_2CF_3$, n=1, $R^7$=H, $R^8$=H)

A solution of 0.46 g (1.8 mM) of the lactone prepared in Example 1f. in 2.0 g (18 mM) of 3,3,3-trifluoro-n-propylamine prepared in Example 21d. was heated in a sealed stainless steel pressure vessel at 190° C. for 24 hours, then concentrated to a white solid. The solid was chromatographed over silica gel using the solvent system of ethyl acetate:hexane (1:1) as the eluent. Recrystallization from toluene/hexane gave 0.39 g (61%) of the title lactam as white crystals, mp=124°–125.5° C.; tlc, $R_f$=0.2, silica gel, ethyl acetate:hexane (1:1).

Elemental Analysis: Calculated for $C_{16}H_{20}N_5F_3O$: C, 54.08; H, 5.67; N, 19.71; Found: C, 53.80; H, 5.66; N, 19.64.

EXAMPLE 22

4-Amino-6,7-dihydro-6-(2-propynyl)-1-n-pentyl-pyrazolo[3,4-b]pyrrolo[3,4-e]pyridin-5(1H)-one (Formula (I), $R^1$=n-pentyl, $R^3$=H, $R^4$=H, D=$NR^6$, $R^6$=$CH_2CCH$, n=1, $R^7$=H, $R^8$=H)

A 50% suspension of NaH in mineral oil (278 mg, 5.78 mM) was washed 3 times with hexane under $N_2$. Freshly distilled THF (50 ml) was added via a syringe. The lactam prepared in Example 15 (1.5 gm, 5.78 mM) was added in one portion to the NaH mixture. The reaction was stirred at 45°–50° C. until $H_2$ evolution ceased (approximately 45 minutes). The solution was cooled to 30° C. and 0.688 g (5.78 mM) of 3-bromo-propyne were added dropwise and the reaction then maintained at 50° C. with stirring for 2 hours. The THF was removed in vacuo and the resulting solid was dissolved in $H_2O$ and extracted with ether. The combined ether layers were washed with saturated NaCl solution, dried over $Na_2SO_4$ and evaporated to leave a yellow solid. This solid was chromatographed over silica gel using ethyl acetate:hexane (1:1) as the solvent system to give 960 mg of the propargyl lactam. The lactam was recrystallized from toluene/hexane as yellow crystals, mp=177°–178° C.; tlc, $R_f$=.3, silica gel, ethyl acetate:hexane (1:1); MS, m/e=297.

Elemental Analysis: Calculated for $C_{16}H_{19}N_5O$: C, 64.62; H, 6.44; N, 23.55; Found: C, 64.78; H, 6.63; N, 23.38.

EXAMPLE 23

4-Amino-6-(3-butenyl)-6,7-dihydro-1-n-pentyl-pyrazolo[3,4-b]pyrrolo[3,4-e]pyridin-5(1H)-one (Formula (I), $R^1$=n-pentyl, $R^3$=H, $R^4$=H, D=$NR^6$, $R^6$=$CH_2CH_2CH$=$CH_2$, n=1, $R^7$=H, $R^8$=H)

A solution of 1.0 gm (3.8 mM) of the lactone prepared in Example 1f. in 5.7 g of 4-aminobut-1-ene was heated in a stainless steel pressure vessel at 190° C. for 15 hours. The excess amine was removed by distillation leaving an amber oil which was chromatographed on a silica gel column with ethyl acetate:hexane (1:1) as the eluting solvent. The title lactam was obtained as a tan solid. This solid was recrystallized from toluene/hexane to leave 0.62 g of the butenyl lactam as off-white crystals, mp=83°–86° C.; tlc, silica gel, $R_f$=0.33, ethyl acetate:hexane (1:1), MS, m/e=313.

Elemental Analysis: Calculated for $C_{17}H_{23}N_5O$: C, 65.15; H, 7.40; N, 22.35; Found C, 64.70; H, 7.66; N, 22.20.

EXAMPLE 24

4-Amino-6,7-dihydro-6-(4-methoxybenzyl)-1-n-pentyl-pyrazolo[3,4-b]pyrrolo[3,4-e]pyridin-5(1H)-one
(Formula (I), $R^1$=n-pentyl, $R^3$=H, $R^4$=H, D=$NR^6$, $R^6$=$CH_2C_6H_4$—p—$OCH_3$, n=1, $R^7$=H, $R^8$=H The procedure of Example 23 was followed with the exception that 1.0 g of the lactone prepared from Example 1f and 12.9 ml of 4-methoxybenzylamine were used as the starting materials. The solution was heated at 185°–200° C. for 15 hours in a sealed stainless steel pressure vessel. The excess amine was distilled off and the residual solid was recrystallized from toluene/hexane to give 1.10 g of the title lactam as off-white crystals, mp=164°–166° C.; tlc, $R_f$=0.3, silica gel, ethyl acetate:-hexane (1:1): MS, m/e=379.

Elemental Analysis: Calculated for $C_{21}H_{25}N_5O$: C, 66.47; H, 6.64; N, 18.46; Found C, 66.46; H, 6.85; N, 18.51.

EXAMPLE 25

4-Amino-6-(4-chlorobenzyl)-6,7-dihydro-1-n-pentyl-pyrazolo[3,4-b]pyrrolo[3,4-e]pyridin-5(1H)-one
(Formula (I), $R^1$=n-pentyl, $R^3$=H, $R^4$=H, D=$NR^6$, $R^6$=$CH_2C_6H_4$—p—Cl, n=1, $R^7$=H, $R^8$=H)

The procedure of Example 23 was followed with the exception that 1.0 g of the lactone prepared in Example 1f and 12 ml of p-chlorobenzylamine were used as the starting materials. The solution was heated in a stainless steel pressure vessel at 185°–200° C. for 15 hours and then concentrated to leave a tan solid. Recrystallization of this solid from toluene/hexane afforded 0.80 g of the title lactam as white crystals, mp=171°–172° C.; tlc, $R_f$=0.55, silica gel, ethyl acetate:hexane (1:1); MS, m/e=383.

Elemental Analysis: Calculated for $C_{20}H_{22}N_5OCl$: C, 62.57; H, 5.78; N, 18.25; Found: C, 62.17; H, 5.90; N, 18.17.

EXAMPLE 26

4-Amino-6,7-dihydro-6-(4-methylbenzyl)-1-n-pentyl-pyrazolo[3,4-b]pyrrolo[3,4-e]pyridin-5(1H)-one
(Formula (I), $R^1$=n-pentyl, $R^3$=H, $R^4$=H, D=$NR^6$, $R^6$=$CH_2C_6H_4$—p—$CH_3$, n=1, $R^7$=H, $R^8$=H)

The procedure of Example 23 was followed with the exception that 1.0 g of the lactone prepared from Example 1f and 12.6 ml of 4-methylbenzylamine were used as the starting materials. The solution was heated at 185°–200° C. for 15 hours in a sealed stainless steel pressure vessel. The excess amine was distilled off leaving a tan solid which was recrystallized from toluene/hexane to give 0.85 g of the title lactam as white crystals, mp=161°–162° C.; tlc, $R_f$=0.39, silica gel, ethyl acetate:hexane (1:1): MS, m/e=363.

Elemental Analysis: Calculated for $C_{21}H_{25}N_5O$: C, 69.39; H, 6.93; N, 19.29; Found: C, 69.34; H, 6.95; N, 18.73.

EXAMPLE 27

4-Amino-6-(3-chlorobenzyl)-6,7-dihydro-1-n-pentyl-pyrazolo[3,4-b]pyrrolo[3,4-e]pyridin-5(1H)-one
(Formula (I), $R^1$=n-pentyl, $R^3$=H, $R^4$=H, D=$NR^6$, $R^6$=$CH_2C_6H_2$—m—Cl, n=1, $R^7$=H, $R^8$=H)

The procedure of Example 23 was followed with the exception that 1.0 g of the lactone prepared in Example 1f. and 12 ml of 3-chlorobenzylazine were used as starting materials. The solution was heated at 185°–200° C. for 15 hours in a stainless steel pressure vessel. The excess amine was distilled off to leave a tan solid. The solid was recrystallized from toluene/hexane to leave 1.0 g of the title lactam as off-white crystals, mp=142°–144° C.; tlc, $R_f$=0.35, silica gel, ethyl acetate:hexane (1:1); MS, m/e=383.

Elemental Analysis: Calculated for $C_{20}H_{22}N_5OCl$: C, 62.57; H, 5.78; N, 18.25; Found: C, 62.51; H, 5.99: N, 18.20.

EXAMPLE 28

4-Amino-6,7-dihydro-1-n-pentyl-6-(3-trifluoromethylbenzyl)pyrazolo[3,4-b]pyrrolo[3,4-e]pyridin-5(1H)-one
(Formula (I), $R^1$=n-pentyl, $R^3$=H, $R^4$=H, D=$NR^6$, $R^6$=$CH_2C_6H_4$—m—$CF_3$, n=1, $R^7$=H, $R^8$=H)

A 50% suspension of NaH in mineral oil (370 mg, 7.7 mM) was washed twice with hexane under $N_2$. Freshly distilled THF (80 ml) was added via syringe. The lactam prepared in Example 15 (2.0 g, 7.7 mM) was added all at once. The mixture was heated at 45° C. for 1 hour. 3-Trifluoromethylbenzyl chloride (1.5 gm) was added all at once via a syringe. The reaction was refluxed for 2 hours and stirred at 25° C. for 15 hours, then filtered and concentrated in vacuo. The residue was taken up in $H_2O$ and extracted with ethyl acetate. The organic layer was washed once with $H_2O$ and once with saturated NaCl solution. The ethyl acetate was removed leaving a yellow solid which was chromatographed on a silica gel column using ethyl acetate:hexane (1:1) as a solvent system. A yellow solid was obtained and recrystallized from toluene/hexane to give the title lactam as yellow crystals, mp=146°–148° C.; tlc, $R_f$=0.25, ethyl acetate:hexane (1:1): MS, m/e=417.

Elemental Analysis: Calculated for $C_{21}H_{22}F_3N_3O$: C, 60.42; H, 5.31; N, 16.78; Found: C, 60.28; H, 5.50; N, 16.72.

EXAMPLE 29

4-Amino-6,7-dihydro-1-n-pentyl-6-(2-phenylethyl)-pyrazolo[3,4-b]pyrrolo[3,4-e]pyridin-5(1H)-one
(Formula (I), $R^1$=n-pentyl, $R^3$=H, $R^4$=H, D=$NR^6$, $R^6$=$CH_2CH_2C_6H_5$, n=1, $R^7$=H, $R^8$=H)

The procedure of Example 23 was followed with the exception that 1.0 g of the lactone prepared in Example 1f. and 13.8 ml of phenylethylamine were used as starting materials. The solution was heated at 185°–200° C. in a stainless steel pressure vessel for 15 hours. The excess amine was distilled off leaving a tan solid which was recrystallized from toluene/hexane to yield 0.99 g of the title lactam as off-white crystals, mp=117°–119° C.: tlc, $R_f$=0.19, silica gel, ethyl acetate:hexane (1:1); MS, m/e=363.

Elemental Analysis: Calculated for $C_{21}H_{25}ON_5.\frac{1}{4}H_2O$: C, 68.55; H, 6.99; N, 19.03; Found: C, 68.65; H, 7.13; N, 19.04.

EXAMPLE 30

4-Amino-6,7-dihydro-6-(2-methoxyethyl)-1-n-pentyl-pyrazolo[3,4-b]pyrrolo[3,4-e]pyridin-5(1H)-one (Formula (I), $R^1$=n-pentyl, $R^3$=H, $R^4$=H, D=$NR^6$, $R^6$=$CH_2CH_2OCH_3$, n=1, $R^7$=H, $R^8$=H)

The procedure of Example 23 was followed with the exception that 1.0 g of the lactone prepared in Example 1f. and 8.6 ml of methoxyethylamine were used as starting materials. The solution was heated at 185°-200° C. for 15 hours in a stainless steel pressure vessel. The excess amine was distilled off to leave a tan solid which was recrystallized from toluene/hexane to yield 0.95 g of the title lactam as off-white crystals, mp=130°-131° C.; tlc, $R_f$=0.37, silica gel, ethyl acetate:hexane (1:1); MS, m/e=317.

Elemental Analysis: Calculated for $C_{16}H_{23}N_5O$: C, 60.54; H, 7.30; N, 22.07; Found: C, 60.47; H, 7.21; N, 22.14.

EXAMPLE 31 a.

4-Ethoxy-6-methyl-1-n-pentyl-1H-pyrazolo[3,4-b]pyridine-5-carboxylic acid ethyl ester A mixture of 12.0 g (41.2 mM) of the hydroxy compound prepared in Example 1b., 12.85 g (82.4 mM) of ethyl iodide and 14.95 g (108.2 mM) of anhydrous potassium carbonate in 63 ml of DMF was stirred at 65°-70° C. for 7 hours. The mixture was cooled, then diluted with 300 ml water and extracted with ether. The combined ether extracts were dried with $MgSO_4$, filtered and concentrated to leave 12.06 g of a light orange oil which was distilled in a Kugelrohr apparatus to give 11.36 g of the product as a light orange oil, bp=130°-140° C. at 0.1-0.2 mm of Hg; tlc, $R_f$=0.4, silica gel, ethyl ether:hexane (1:1); MS, m/e=319.

The following is an alternative preparation of this product.

To a cold (ice bath) stirred solution of 32.57 g (105.1 mM) of the chloro compound prepared in Example 1c in 75 ml of absolute ethanol was added dropwise an ethanolic solution of sodium ethoxide prepared by dissolving 2.59 g (112.5 mg atoms) of sodium in 60 ml of absolute ethanol. After the addition was complete, the ice bath was removed and the reaction mixture was stirred 0.5 hour at room temperature and then 2 hours at reflux. The cooled reaction mixture was concentrated and the residue diluted with ethyl ether and water. The ether layer was separated, washed once with water, dried with $MgSO_4$, then filtered and concentrated to leave 31.58 g of a yellow oil. Distillation of the oil gave 30.37 g of the product as a light yellow oil, bp=130°-140° C. at 0.5 mm of Hg. The tlc and MS of this material are identical to those of the material prepared above.

b.

5-Carboethoxy-4-ethoxy-1-n-pentyl-1H-pyrazolo[3,4-b]pyridin-6-yl acetic acid (Formula (XVI), $R^1$=n-pentyl, $R^3$=H, $R^{15}$=$CH_2CH_3$, R=$CH_2CH_3$, $R^7$=H, $R^8$=H, $R^{16}$=COOH)

To a cold (−78° C.) stirred solution of 0.38 g (3.8 mM) of diisopropyl amine in 16 ml of anhydrous THF under a nitrogen atmosphere were added 1.74 ml (3.82 mM) of 2.20 molar butyllithium in hexane. After being stirred at −78° C. for 20 minutes, the resulting cold solution of lithium diisopropylamide was added dropwise under a nitrogen atmosphere to a cold (−78° C.) stirred solution of 1.16 g (3.63 mM) of the 4-ethoxy compound of Example 31a. A red color developed during this addition. After the addition was complete, the resulting deep red solution was stirred at −78° C. for an additional 30 minutes and then poured onto dry ice. After the dry ice had evaporated, the resulting solution was concentrated. The residue was diluted with water and the resulting mixture washed with ether. The aqueous layer was then acidified carefully with 10% aqueous hydrochloric acid whereupon a white precipitate formed. This was collected and air-dried to give 0.82 g of a white solid. Recrystallization of this solid from toluene/hexane gave 0.67 g of the product as white crystals, mp=122.5° C. (gas evolution); MS, m/e=363.

Elemental Analysis: Calculated for $C_{18}H_{25}N_3O_5$: C, 59.49; H, 6.93; N, 11.56; Found: C, 59.47; H, 6.80; N, 11.45.

c.

4-Ethoxy-6-(2-hydroxyethyl)-1-n-pentyl-1H-pyrazolo[3,4-b]pyridine-5-carboxylic acid ethyl ester (Formula (XVI), $R^1$=n-pentyl, $R^3$=H, $R^{15}$=$CH_2CH_3$, R=$CH_2CH_3$, $R^7$=H, $R^8$=H, $R^{16}$=$CH_2OH$)

1.70 ml (16.7 mM) of borane methyl sulfide complex were added under a nitrogen atmosphere to a cold stirred solution of 4.20 g (11.6 mM) of the carboxylic acid prepared in Example 31b. in 45 ml of anhydrous THF. An evolution of gas occurred. The reaction mixture was stirred at 0° C. for 0.25 hour, then at 25° C. for 0.5 hour and finally at reflux for 3 hours. The cooled reaction mixture was carefully quenched with about 4 ml of methanol and then concentrated to leave a green oil. This oil was taken up in ether and the resulting solution washed with aqueous sodium bicarbonate, dried with $MgSO_4$, filtered and concentrated to leave 3.54 of a light green oil which was chromatographed over silica gel using acetone:hexane (1.5:8.5) as the eluant. The fractions containing the desired hydroxyethyl compound were combined and concentrated to leave 2.00 g of the desired product as a pale yellow oil; tlc, $R_f$=0.3, silica gel, acetone:hexane (1:4); MS, m/e=349.

d.

4-Amino-7,8-dihydro-1-n-pentyl-1H,5H-pyrano[4,3-b]pyrazolo[4,3-e]pyridine-5-one (Formula (I), $R^1$=n-pentyl, $R^3$=H, $R^4$=H, D=O, n=2, $R^7$=H, $R^8$=H)

A solution of 2.0 g (5.7 mM) of the hydroxyethyl compound prepared in Example 31c. in 20 ml of anhydrous liquid ammonia was heated in a sealed stainless steel pressure vessel at 100°-110° C. for 12 hours. The ammonia was then allowed to evaporate and the white solid residue was passed through a short column of silica gel using 2% methanol in methylene chloride as the eluant. The fractions containing the desired product were combined and concentrated to leave 1.82 g of a white solid. Recrystallization of this solid from toluene gave 1.26 g of the desired lactone as white plates, mp=193.5°-194.5° C.; tlc, $R_f$=0.7, silica gel, chloroform:methanol (93:7): MS, m/e=274.

Elemental Analysis Calculated for $C_{14}H_{18}H_4O_2$: C, 61.30; H, 6.61; N, 20.43; Found: C, 61.22; H, 6.73; N, 20.33.

EXAMPLE 32

4-Amino-7,8-dihydro-1-n-pentyl-6-n-propyl-1H-pyrazolo[3,4-b][1,6]naphthyridin-5(6H)-one hydrochloride (Formula (I), $R^1$=n-pentyl, $R^3$=H, $R^4$=H, D=$NR^6$, $R^6$=n-propyl, n=2, $R^7$=H, $R^8$=H)

A solution of 0.58 g (2.1 mM) of the lactone prepared in Example 31d. in 15 ml of n-propylamine was heated in a stainless steel pressure vessel at 230°–250° C. for 12 hours. The cooled reaction mixture was concentrated to leave a yellow gum which was chromatographed over silica gel using ethyl acetate: hexane (1:1) as the eluant. The fractions containing the desired product were combined and concentrated to leave 0.26 g of the lactam as a pale yellow gum. This material was combined with 0.1 g of identical material from a previous preparation and both dissolved in 4 ml of ethanol which was then acidified with ethereal hydrogen chloride. The resulting white precipitate was collected, washed with cold ethanol:ethylether (2:1) and then ether, and air-dried to give 0.28 g of the desired lactam product as white needles, mp=262°–265° C. (slow decomposition): MS of the free base, m/e=315.

Elemental Analysis Calculated for $C_{17}H_{25}N_5O.HCl.0.2H_2O$: C, 57.44; H, 7.49; N, 19.70; Found: C, 57.43; H, 7.31; N, 19.66.

EXAMPLE 33

4-Amino-7,8-dihydro-6-ethyl-1-n-pentyl-1H-pyrazolo[3,4-b][1,6]- naphthyridin-5(6H)-one hydrochloride (Formula (I), $R^1$=n-pentyl, $R^3$=H, $R^4$=H, D=$NR^6$, $R^6$=$CH_2CH_3$, n=2, $R^7$=H, $R^8$=H)

A solution of 0.70 g (2.6 mM) of the lactone prepared in Example 31d. in 25 ml of ethylamine was heated in a stainless steel pressure vessel at 230°–250° C. for 22 hours. The reaction mixture was concentrated and the residue dissolved in 4 ml of ethanol which was then acidified with ethereal hydrogen chloride to form a white crystalline precipitate. The mixture was diluted with 2 ml of ether and filtered to separate the crystals. After quickly washing the crystals with cold ethanol:ether (1:1), they were air-dried to give 0.21 g of the desired product as white crystals, mp=243°–250° C.; MS, m/e=301.

Elemental Analysis Calculated for $C_{16}H_{23}N_5O.HCl$: C, 56.88; H, 7.16; N, 20.73; Found: C, 56.91; H, 7.22; N, 20.44.

EXAMPLE 34

4-Amino-6,7-dihydro-6-(3-methoxypropyl)-1-n-pentyl-pyrazolo[3,4b]pyrrolo[3,4-e]pyridin-5(1H)-one (Formula (I), $R^1$=n-pentyl, $R^3$=H, $R^4$=H, D=$NR^6$, $R^6$=$(CH_2)_3OCH_3$, n=1, $R^7$=H, $R^8$=H)

The procedure of Example 23 was followed with the exception that 1.80 g (6.92 mM) of the lactone prepared in Example 1f. and 15 ml of 3-methoxypropylamine were used as starting materials. The solution was heated in a stainless steel pressure vessel at 185°–195° C. for 12 hours and then concentrated to leave a tan solid. This solid was chromatographed over silica gel using 3% methanol in methylene chloride as the eluant. The product was obtained as a tan solid which was recrystallized twice from toluene/hexane to give 1.45 g of white crystals, mp=143°–144° C.; tlc, $R_f$=0.6, silica gel, chloroform:methanol (93:7): MS, m/e=331.

Elemental Analysis Calculated for $C_{17}H_{25}N_5O_2$: C, 61.61; H, 7.60; N, 21.13 ;Found: C, 61.33; H, 7.62; N, 21.39.

EXAMPLE 35

4-Amino-6-(2-ethoxyethyl)-6,7-dihydro-1-n-pentyl-pyrazolo[3,4-b]pyrrolo[3,4-e]pyridine-5(1H)-one (Formula (I), $R^1$=n-pentyl, $R^3$=H, $R^4$=H, D=$NR^6$, $R^6$=$(CH_2)_2OCH_2CH_3$, n=1, $R^7$=H, $R^8$=H)

The procedure of Example 23 was followed with the exception that 1.80 g (6.92 mM) of the lactone prepared in Example 1f. and 12 ml of 2-ethoxyethylamine were used as starting materials. The solution was heated in a stainless steel pressure vessel at 180°–190° C. for 12 hours, then cooled and poured into water. The precipitate was collected, washed with water and air-dried. The resulting tacky solid was dissolved in 20 ml of hot toluene, treated with a few grams of silica gel, filtered hot, then allowed to cool. The resulting precipitate was collected, washed with cold toluene, and air-dried to give 1.45 g of the desired product as white crystals, mp=170°–171° C.: tlc, $R_f$=0.6, silica gel, chloroform:methanol (93:7): MS, m/e=331.

Elemental Analysis Calculated for $C_{17}H_{25}N_5O_2$: C, 61.61; H, 7.60; N, 21.13; Found: C, 61.58; H, 7.41; N, 20.90.

EXAMPLE 36 a. [[(1-n-pentyl-5-pyrazolyl)amino]methylene]malonic acid diethylester (Formula (XI), $R^1$=n-pentyl, $R^3$=H, $R^{12}$=$CH_2CH_3$)

A mixture of 24.75 g (161.5 mM) of 5-amino-1-n-pentylpyrazole and 34.97 g (161.5 mM) of diethylethoxymethylene malonate was heated under $N_2$ at 120° C. for 2 hours. The ethanol which evolved was collected in a Dean-Stark trap. The crude mixture was distilled in a Kugelrohr apparatus to give 45.46 g of the product as a yellow oil, bp=146°–149° C. at 0.05–0.06 mm of Hg: tlc, $R_f$=0.7, silica gel, ethylacetate:hexane (1:1); MS, m/e=323.

b.

4-Hydroxy-1-n-pentyl-1H-pyrazolo[3,4-b]pyridine-5-carboxylic acid ethyl ester (Formula (XII), $R^1$=n-pentyl, $R^3$=H, $X^1$=OH, $R^{12}$=$CH_2CH_3$, $R^{13}$=H)

The diester product of Example 36a. (45.04 g, 139.3 mM) was dissolved in 111 ml of diphenylether and heated for 2 hours under $N_2$ at 235°–255° C. The diphenylether was removed under water aspirator vacuum while the mixture was still warm. The residue was distilled in a Kugelrohr to give 37.16 g of the product as a clear oil which crystallized. The solid was recrystallized from hexane to yield 18.40 g of white plates, mp=67.0°–69.8° C.; mp of unrecrystallized solid =54°–70° C.; tlc, $R_f$=0.5, silica gel, methylene chloride:methanol (97:3); MS, m/e=277.

c.

4-Chloro-1-n-pentyl-1H-pyrazolo[3,4-b]pyridine-5-carboxylic acid ethyl ester

The hydroxy product of Example 36b. (17.26 g, 62.24 mM) was taken up in 78 ml of phosphorus oxychloride (129 g, 840 mM) and refluxed for 0.8 hours. The phosphorus oxychloride was removed under water aspirator vacuum and the residue was treated with cold water then with sodium bicarbonate until the mixture was basic. The mixture was extracted with ether and the extract dried over anhydrous magnesium sulfate then filtered and concentrated to yield 18.61 g of the product as a yellow oil; tlc, $R_f=0.8$, silica gel, ether:hexane (1:1): MS, m/e=295.

d. 4-Chloro-1-n-pentyl-1H-pyrazolo[3,4-b]pyridine-5-carboxlic acid ethyl ester-7-oxide To a solution of 16.8 ml (25.0 g, 119 mM) of trifluoroacetic anhydride in 66 ml of methylene chloride, cooled in an ice-water bath, was added 90% hydrogen peroxide (2.7 ml, 3.4 g, 100 mM) over a 2 minute period. The mixture was stirred for fifteen minutes then allowed to warm to room temperature. A solution of 19.5 g (66.13 mM) of the chloro compound prepared in Example 36c in 66 ml of methylene chloride was added over a 10 minute period while the temperature of the mixture was maintained at 30°-35° C. in a water-ice bath. After being kept 2 hours at room temperature, the mixture was poured into 800 ml of water with stirring. The mixture was treated with a solution of 12.8 g of sodium sulfite in 120 ml of water in portions (exotherm). Solid sodium bicarbonate was then added in portions with stirring until the mixture was slightly basic. The mixture was extracted three times with methylene chloride and the organic phase was dried over anhydrous magnesium sulfate, then filtered and concentrated to give 19.96 g of a crude mixture of product and starting material as an amber oil which crystallized to a tan solid. The solid was flash chromatographed on silica gel using ether:hexane (1:1) as the eluant to give 13.57 g of an off-white solid corresponding to the N-oxide and 4.25 g of an oil corresponding to the starting material. The N-oxide was recrystallized from hexane to give 12.04 g of a white, crystalline solid, mp=50.0°-52.3° C.; tlc, $R_f=0.3$, silica gel, ether:hexane (1:1): MS, m/e=311.

Elemental Analysis Calculated for $C_{14}H_{18}ClN_3O_3$: C, 53.93; H, 5.82; N, 13.48; Found: C, 53.65; H, 5.87; N, 13.42.

e. 4-Ethoxy-7-oxide-1-n-pentyl-1H-pyrazolo[3,4-b]pyridine-5carboxylic acid ethyl ester (Formula (XIIA), $R^1$=n-pentyl, $R^3$=H, $X^{11}$=OCH$_2$CH$_3$, $R^{12}$=CH$_2$CH$_3$, $R^{13}$=H)

A solution of 8.05 g (25.8 mM) of the N-oxide prepared in Example 36d in 40 ml of ethanol which had been dried over 4 Angstrom molecular sieves was cooled to 8°-12° C. and treated for 20 minutes at 8°-12° C. with a freshly prepared solution of sodium ethoxide (27.6 mM) in 13.8 ml of ethanol. The mixture was allowed to warm to room temperature over a 3 hour period, then concentrated to a yellow solid which was suspended/dissolved in ethylacetate/water. The ethylacetate solution was dried over anhydrous magnesium sulfate, filtered, and concentrated to give the crude product as 6.01 g of a light yellow solid. The solid was flash chromatographed on silica gel using ethyl acetate as the eluent to give 5.17 g of the desired product as white solid. 1.17 g were recrystallized from toluene:hexane to give 0.75 g of a white solid, mp=103.5°-106.0° C.; tlc, $R_f=0.3$, silica gel, ethyl acetate; MS, m/e=321.

Elemental Analysis Calculated for $C_{16}H_{23}N_3O_4$: C, 59.80; H, 7.21 N, 13.08; Found: C, 59.68; H, 7.20; N, 13.05.

f. 6-Bromo-4-ethoxy-1-n-pentyl-1H-pyrazolo[3,4-b]pyridine-5carboxylic acid ethyl ester To a solution of 1.14 g (3.55 mM) of the N-oxide prepared in Example 36e. in 1.3 ml of chloroform were added 3.8 g of solid phosphorus oxybromide at room temperature (effervescence). The mixture was slowly heated to reflux in an oil bath over a 0.5 hour period. After being refluxed for 1 hour, the mixture was allowed to cool to room temperature then poured into about 100 ml of H$_2$O, stirred for 5 minutes, treated with sodium bicarbonate until basic and extracted three times with ether. The ether extracts were dried over anhydrous magnesium sulfate, filtered and concentrated to give 1.43 g of a light amber oil. The oil was dissolved in about 5 ml of hexane and cooled in dry ice/acetone to yield the product as 0.88 g of off-white crystals, mp=42.5°-46.5° C.; tlc, $R_f=0.4$, silica gel, ether:hexane (1:1): MS, m/e=383.

Elemental Analysis Calculated for $C_{16}H_{22}BrN_3O_3$: C, 50.01: H, 5.77: N, 10.94; Found C, 50.13: H, 5.76: N, 10.91.

g. 1,7-Dihydro-4-ethoxy-7-methyl-1-n-pentyl-5H-furo[3,4-b] pyrazolo[4,3-e]pyridin-5(1H)-one A solution of 1.54 g (4.01 mM) of the bromo product of Example 36f. in 27 ml of dry THF and 7 ml of dry hexane was cooled under a nitrogen atmosphere to −85° to −90° C. (cold bath, hexane:acetone:isopropanol (4:1:1)/liquid nitrogen). n-Butyllithium in hexane (2.13 ml of a 1.92 molar solution, 4.09 mM, 1.02 equivalents) was added to the cold solution over a 2 minute period with vigorous stirring. The solution became orange. After 5 minutes, 0.4 ml (7 mM) of acetaldehyde (freshly distilled at room temperature under N$_2$) were added in one portion. The solution was allowed to warm to 2° C. then quenched with 1.8 ml of water. The mixture was dried over anhydrous magnesium sulfate, filtered and concentrated to yield 1.35 g of a white solid which was dissolved in the minimum amount of toluene, filtered, and treated with an equal volume of hexane. The resulting white solid was collected at room temperature to give 0.82 g of the title compound, mp=94.0°-97.0° C.; tlc, $R_f=0.3$, silica gel, ether:hexane (1:1): MS, m/e=303.

Elemental Analysis Calculated for $C_{16}H_{21}N_3O_3$: C, 63.35; H, 6.98; N, 13.85; Found: C, 63.09; H, 7.05; N, 13.96.

h. 4-Amino-1,7-dihydro-7-methyl-1-n-pentyl-5H-furo[3,4-b]pyrazolo[4,3-e]pyridin-5(1H)-one (Formula (I), $R^1$=n-pentyl, $R^3$=H, $R^4$=H, D=0, n=1, $R^7$=CH$_3$, $R^8$=H)

0.94 g (3.1 mM) of the product of Example 36g. were suspended in about 20 ml of liquid ammonia (condensed via dry ice trap) and sealed in a stainless steel bomb. The mixture was allowed to stand at room temperature for 24 hours and the excess ammonia then evaporated to leave 0.85 g of a white solid.

A portion (0.65 g) of the product was chromatographed on silica gel using ethyl acetate as the eluent to yield 0.59 g of a white solid which, on recrystallization from toluene gave 0.55 g of brilliant white plates, mp=214.5°-215.0° C.; tlc, R_f=0.4, silica gel, ether; MS, m/e=274.

Elemental Analysis Calculated for $C_{14}H_{18}N_4O_2$: C, 61.30; H, 6.61; N, 20.43; Found: C, 61.26; H, 6.63; N, 20.57.

EXAMPLE 37
4-Amino-6,7-dihydro-7-methyl-1-n-pentyl-6-n-propyl-pyrazolo[3,4-b]pyrrolo[3,4-e]pyridin-5(1H)-one hydrochloride (Formula (I), $R^1$=n-pentyl, $R^3$=H, $R^4$=H, D=NR$^6$, $R^6$=CH$_2$CH$_2$CH$_3$, n=1, $R^7$=CH$_3$, $R^8$=H)

The lactone prepared in Example 36h. (0.85 g, 31mM) was taken up in approximately 20 ml of n-propylamine and heated in a stainless steel bomb at 245°-250° C. for 24 hours. The mixture was cooled to room temperature and concentrated to give 1.1 g of a tan solid. The solid was chromatographed on silica gel using ether as the eluent to give 0.24 g of a colorless oil. The oil was taken up in 5 ml of ether, treated with ethereal hydrogen chloride and filtered to give a white solid. The solid was recrystallized from a minimum amount of ethanol diluted with an equal volume of ether to give the desired product hydrochloride as 0.16 g of a white solid, mp=189°-193° C.; tlc, R_f=0.3, sample dissolved in ethanol with triethylamine added, silica gel, ether; MS, m/e=315.

Elemental Analysis Calculated for $C_{17}H_{25}N_5O.HCl$: C, 58.03; H, 7.45; N, 19.90; Found: C, 58.11; H, 7.39; N, 19.76.

EXAMPLE 38 a.
1,7-Dihydro-7,7-dimethyl-4-ethoxy-1-n-pentyl-5H-furo[3,4-b]pyrazolo[4,3-e]pyridin-5(1H)-one The 6-lithium compound was prepared as indicated in the beginning of Example 36g. using 1.78 g (4.63 mM) of the 6-bromo compound prepared in Example 36f. To the cold (−85° to −90° C.) anion solution was added 0.51 ml (0.40 g, 6.9 mM) of dry acetone in one portion. The mixture was slowly warmed to −10° C. and 1.1 ml, (25 equivalents) water was added. The mixture was warmed to room temperature, dried over anhydrous magnesium sulfate, filtered, and concentrated to give 1.60 g of a white solid which was recrystallized from toluene/hexane to give the final product as 1.14 g of a white crystalline solid, mp=111.0°-111.8° C.: tlc, R_f=0.3, silica gel, ether:hexane (1:1); MS, m/e=317.

Elemental Analysis Calculated for $C_{17}H_{23}N_3O_3$: C, 64.33; H, 7.30; N, 13.24; Found: C, 64.24; H, 7.33; N, 12.98.

b.
4-Maino-1,7-dihydro-7,7-dimethyl-1-n-pentyl-5H-furo[3,4-b]

pyrazolo[4,3-e]pyridin-5(1H)-one (Formula (I), $R^1$=n-pentyl, $R^3$=H, $R^4$=H, D=O, n=1, $R^7$=CH$_3$, $R^8$=CH$_3$)

1.42 g (4.47 mM) of the ethoxy product of Example 38a. were suspended in about 20 ml of liquid ammonia (condensed via dry ice trap) and sealed in a stainless steel bomb. The mixture was allowed to stand at room temperature for 24 hours. The excess ammonia was evaporated to leave a white solid. The solid was recrystallized from toluene/hexane to yield the product as 1.24 g of a white solid, mp=162.7°-164.0° C.; tlc, R_f=0.5, silica gel, ether: MS, m/e=288.

Elemental Analysis Calculated for $C_{15}H_{20}N_4O_2$: C, 62.48; H, 6.99; N, 19.43; Found: C, 62.36; H, 6.76; N, 19.55.

EXAMPLE 39
4-n-Butylamino-1,7-dihydro-7,7-dimethyl-1-n-pentyl-5H-furo[3,4-b]pyrazolo[4,3-e]pyridin-5(1H)-one (Formula (I), $R^1$=n-pentyl, $R^3$=H, $R^4$=(CH$_2$)$_3$CH$_3$, D=O, n=1, $R^7$=CH$_3$, $R^8$=CH$_3$)

EXAMPLE 38b.

The primary amine prepared in (0.70 g, 2.4 mM) was heated in a stainless steel bomb with 15 ml (11 g, 150 mM) of n-butylamine at 265°-270° C. for 30 hours then cooled to room temperature. The mixture was concentrated to yield 1.01 g of an amber oil which later crystallized to a tan solid. The solid was recrystallized from toluene:hexane (1:3) to give 0.27 g of unreacted starting material as an off-white solid. The filtrate from the above recrystallization was concentrated to give 0.68 g of an amber oil which was chromatographed on silica gel using hexane:ether (2:1) as the eluent to yield 0.42 g of a clear oil. The oil was crystallized from hexane (dry ice/acetone bath) to give 0.32 g of the title compound as a white solid, mp=77.5°-79.5° C.; tlc, R_f=0.4, silica gel, ether:hexane (1:1), MS, m/e=344.

Elemental Analysis Calculated for $C_{19}H_{28}N_4O_2$: C, 66.25; H, 8.19; N, 16.27; Found: C, 66.17; H, 7.98; N, 16.18.

EXAMPLE 40
4-Amino-6-(3,4-dichlorobenzyl)-6,7-dihydro-1-n-pentylpyrazolo-[3,4-b]pyrrolo[3,4-e]pyridin-5(1=H)-one (Formula (I), $R^1$=n-pentyl, $R^3$=H, $R^4$=H, D=NR$^6$, $R^6$=CH$_2$C$_6$H$_3$-m,p-diCl, n=1, $R^7$=H, $R^8$=H)

15 ml of 93% pure 3,4-dichlorobenzylamine (100 mM, 26 equivalents) were added to 1.01 g (3.88 mM) of the lactone product of Example 1f. and the mixture was heated in a stainless steel bomb at 180°-185° C. for 12 hours then cooled to room temperature. The excess dichlorobenzylamine was distilled off in a Kugelrohr apparatus at 100°-110° C., 0.05-0.06 mm of Hg to leave 3.23 g of a tan solid residue. The solid was recrystallized from the minimum amount of toluene to yield 0.86 g of the desired product as an off-white solid, mp=175°-179° C.; tlc, R_f=0.5, silica gel, ethyl acetate; MS, m/e=417.

Elemental Analysis Calculated for $C_{20}H_{21}Cl_2N_5O$: C, 57.42; H, 5.06; N, 16.74; Found: C, 57.17; H, 5.10; N, 17.01.

EXAMPLE 41 a.
1,7-dihydro-4-ethoxy-1-n-pentyl-7-phenyl-5H-furo[3,4-b]pyrazolo[4,3-e]pyridin-5(1H)-one The 6-lithium compound was prepared as indicated in Example 36g. using 1.32 g (3.43 mM) of the 6-bromo compound prepared in Example 36f. 0.39 ml (0.40 g, 3.8 mM) of benzaldehyde freshly distilled from Zn dust under N$_2$ were added in one portion to the cold (−85° to −90° C.) anion solution. The mixture was slowly warmed to 0° C. and 1.5 ml (25 equivalents) of water were added. The mixture was filtered to give 0.19 g of a white solid. The filtrate was dried over anhydrous magnesium sulfate, filtered, and concentrated to give 1.54 g of a light-yellow oil. The oil was chromatographed on silica gel using ether:hexane (3:2) as the eluent to give 0.35 g of a white solid, mp=141.0°–143.3° C. Tlc indicated that the original solid from the reaction mixture was the same material obtained from the chromatography; tlc, $R_f=0.3$, silica gel, ether:hexane (3:2); MS, m/e=365.

b. 4-Amino-1,7-dihydro-1-n-pentyl-7-phenyl-5H-furo[3,4-b]pyrazolo[4,3-e]pyridin-5(1H)-one (Formula (I), $R^1$=n-pentyl, $R^3$=H, $R^4$=H, D=O, n=1, $R^7$=$C_6H_5$, $R^8$=H)

The 4-ethoxy compound prepared in Example 41a. (0.52 g, 1.4 mM) was suspended in about 7 ml of liquid ammonia (condensed via dry ice trap) and sealed in a stainless steel bomb. The mixture was allowed to stand at room temperature for 24 hours. The excess ammonia was evaporated to leave a light-pink, crystalline solid which was chromatographed on silica gel using ether as the eluent to give 0.40 g of a white solid. A 0.05 g portion of the solid was recrystallized from toluene/hexane to give 0.04 g of a white solid, mp=190.5°–191.2° C.; tlc, $R_f=0.5$, silica gel, ether; MS, m/e=336.

Elemental Analysis Calculated for $C_{19}H_{20}N_4O_2$: C, 67.84; H, 5.99; N, 16.66; Found: C, 67.60; H, 6.00; N, 16.45.

EXAMPLE 42

6,7-Dihydro-1-n-pentyl-4-propionamido-6-n-propyl-pyrazolo[3,4-b]pyrrolo[3,4-e]pyridin-5(1H)-one.hydrochloride (Formula (I), $R^1$=n-pentyl, $R^3$=H, $R^4$=$COCH_2CH_3$, D=$NR^6$, $R^6$=$CH_2CH_2CH_3$, n=1, $R^7$=H, $R^8$=H)

A mixture of 0.98 g (3.3 mM) of the primary amine prepared in Example 5 and 0.40 g (3.3 mM) of p-dimethylaminopyridine in 16 ml dry toluene was treated with 4.1 ml (4.2 g, 32 mM, 10 equivalents) of propionic anhydride at room temperature. The solution was refluxed for 5.5 hours, poured into 300 ml of $H_2O$, basified with sodium bicarbonate, then stirred for 20 minutes at room temperature. The mixture was extracted three times with ether and the ether extracts were dried over anhydrous magnesium sulfate, filtered and concentrated to yield 1.20 g of a clear, yellow oil. The oil was chromatographed on silica gel using ether:hexane (2:1) as the eluent to give 0.93 g of a clear oil. The oil was dissolved in ether and treated with ethereal hydrogen chloride to give a white solid which was recrystallized from ethanol (5 ml)/ether (15 ml) to give 0.93 g of the desired product as a white solid, mp=115°–121° C.; tlc, $R_f=0.6$, sample in ethanol with triethylamine, silica gel, ether; MS, m/e=357.

Elemental Analysis Calculated for $C_{19}H_{27}N_5O_2.HCl$: C, 57.93; H, 7.16; N, 17.78; Found: C, 57.71; H, 7.08; N, 17.99.

EXAMPLE 43

4-n-Butyramido-6,7-dihydro-1-n-pentyl-6-n-propyl-pyrazolo[3,4-b]pyrrolo[3,4-e]pyridin-5(1H)-one hydrochloride (Formula (I), $R^1$=n-pentyl, $R^3$=H, $R^4$=$CO(CH_2)_2CH_3$, D=$NR^6$, $R^6$=$CH_2CH_2CH_3$, n=1, $R^7$=H, $R^8$=H)

A mixture of 0.95 g (3.1 mM) of the primary amine prepared in Example 5 and 0.38 g (3.1 mM) of p-dimethylaminopyridine in 16 ml dry toluene was treated with 5.2 ml (5.0 g, 32 mM) of n-butyric anhydride under nitrogen at room temperature. The mixture was refluxed for 8 hours and then worked up as described in Example 42. The resulting 3.37 g of yellow liquid was flash chromatographed on silica gel using ether as the eluent to give 1.62 g of a yellow oil which was taken up in ether and treated with ethereal HCl. The solid was collected and air dried to give 1.18 g of product which was recrystallized from ethanol/ether (1:3) to give 0.91 g of the title compound as a white solid, mp=129°–139° C.; tlc, $R_f=0.4$, silica gel, ether:hexane (1:1): MS, m/e=371.

Elemental Analysis Calculated for $C_{20}H_{29}N_5O_2.HCl$: C, 58.88; H, 7.41; N, 17.17; Found: C, 58.95; H, 7.58; N, 17.28.

EXAMPLE 44

4-Benzamido-6,7-dihydro-1-n-pentyl-6-n-propyl-pyrazolo[3,4-b]pyrrolo[3,4-e]pyridin-5(1H)-one (Formula (I), $R^1$=n-pentyl, $R^3$=H, $R^4$=$COC_6H_5$, D=$NR^6$, $R^6$=$CH_2CH_2CH_3$, n=1, $R^7$=H, $R^8$=H)

A mixture of 0.96 g (3.2 mM) of the primary amine prepared in Example 5 and 0.39 g (3.2 mM) of p-dimethylaminopyridine in 16 ml of dry toluene was treated with 7.22 g (31.9 mM) of benzoic anhydride under $N_2$ at room temperature. The mixture was heated at reflux for 1.4 hours. A further 0.39 g (3.2 mM) of p-dimethylaminopyridine was added and the mixture was heated at reflux for an additional 8 hours then cooled to room temperature and worked up as described in Example 42 to give 3.23 g of an off-white solid containing some benzoic anhydride. The solid was flash chromatographed on silica gel using hexane:ethyl acetate (2:1) as the eluent to give 1.14 g of a white solid. The solid was recrystallized from toluene/hexane to give 0.91 g of the title compound as white solid plates, mp=124.8°–125.7° C.; tlc, $R_f=0.6$, silica gel, ethyl acetate:hexane (1:1); MS, m/e=405.

Elemental Analysis Calculated for $C_{23}H_{27}N_5O_2$: C, 68.12; H, 6.71; N, 17.27; Found: C, 68.07; H, 6.61; N, 17.11.

EXAMPLE 45 a. 4,4,4-Trifluorobutanol 36.0 g (255 mM) of the carboxylic acid prepared in Example 21c. were added dropwise to a stirred suspension of 11.6 g (306 mM) of lithium aluminum hydride in 300 ml of ethyl ether at −78° C. After the addition was completed, the reaction mixture was allowed to warm to room temperature and stirred an additional 18 hours. After being cooled to 0° C., the reaction mixture was quenched with solid sodium sulfate decahydrate. The reaction mixture was filtered and the solids were collected and washed with ether. The combined organic material including filtrate and washes was concentrated to leave 43.6 g of the desired alcohol as a colorless liquid.

b. 1-Bromo-4,4,4-trifluorobutane 5.23 ml (102 mM) of bromine were added dropwise to a stirred solution of 26.7 g (102 mM) of triphenylphosphine in 170 ml of methylene chloride. A precipitate formed. 10.8 g (85 mM) of the alcohol prepared in Example 45a. were added dropwise to the resulting stirred suspension cooled to 0° C. The resulting solution was stirred at 0° C. for 2 hours. 0.69 ml of methanol were added followed by about 125 ml of pentane, whereupon a precipitate formed. The resulting mixture was refluxed for 30 minutes, then cooled and filtered. The filtrate was concentrated carefully and the residue distilled to give 7.22 g of the desired bromo compound as a colorless liquid, bp=55° C. at 100 mm of Hg.

c.
4-Chloro-6-methyl-1H-pyrazolo[3,4-b]pyridine-5-carboxylic acid ethyl ester (Formula (VI), $R^1$=H, $R^3$=H, X=Cl, R=$CH_2CH_3$, $R^7$=H, $R^8$=H)

A mixture of 10.0 g (37.4 mM) of 4-chloro-1-ethyl-6-methyl-1H-pyrazolo[3,4-b]pyridine-5-carboxylic acid ethyl ester, prepared according to Examples 1b. and 1c. from 5-amino-1-ethylpyrazole in place of 5-amino-1-pentylpyrazole, and 7.65 g (43.0 mM) of N-bromosuccinimide in 75 ml of carbon tetrachloride was illuminated with a sunlamp and stirred under $N_2$ at gentle reflux for 2 hours. The cooled reaction mixture was filtered and the filtrate concentrated to leave an orange residue which was dissolved in 50 ml of THF. 35 ml of saturated aqueous sodium carbonate were added, and the mixture was stirred vigorously at room temperature for 18 hours and then diluted with water and extracted with ethyl acetate. The combined extracts were dried with $MgSO_4$, filtered and concentrated to leave a white solid which was chromatographed over silica gel using the solvent system of ethyl acetate:hexane (1:3) as the eluant. The fractions containing the desired product were combined and concentrated to leave a white solid. Recrystallization of the solid from toluene/hexane gave 4.88 g of the desired ester as white needles, mp=156°-157.5° C.; tlc, $R_f$=0.2, silica gel, ethyl acetate:hexane (1:3).

d.
4-Chloro-6-methyl-1-(4,4,4-trifluoro-n-butyl)-1H-pyrazolo[3,4-b]pyridine-5-carboxylic acid ethyl ester (Formula (VI), $R^1$=$(CH_2)_3CF_3$, $R^3$=H, X=Cl, R=$CH_2CH_3$, $R^7$=H, $R^8$=H)

A mixture of 12.2 g (50.9 mM) of the chloro compound prepared in Example 45c., 14.1 g (102 mM) of powdered anhydrous potassium carbonate and 10.6 g (56.0 mM) of the bromo compound prepared in Example 45b., in 75 ml of DMF was stirred vigorously for 2.5 hours under a nitrogen atmosphere. The reaction mixture was poured into water and extracted with ether. The combined ether extracts were dried with $MgSO_4$, filtered and concentrated to leave a brown oil which was chromatographed over silica gel using the solvent system ethyl acetate:hexane (1:3) as the eluant. The fractions containing the desired material were combined and concentrated to leave 14.7 g of the title chloro compound as a white solid; tlc, $R_f$=0.6, silica gel, ethyl acetate:hexane (1:3).

e.
4-Chloro-6-methyl-1-(4,4,4-trifluoro-n-butyl)-7-oxide-1H-pyrazolo[3,4-b]pyridine-5-carboxylic acid ethyl ester (Formula (VII), $R^1$=$(CH_2)_3CF_3$, $R^3$=H, X=Cl, R=$CH_2CH_3$, $R^7$=H, $R^8$=H)

The title compound was prepared according to the procedure of Example 19b. using the 1-trifluorobutyl derivative prepared in the above Example 45d. in place of the 1-(3-methylbutyl) derivative. The oxide was obtained as a clear oil; tlc, $R_f$=0.3, silica gel, ethyl acetate:hexane (1:3).

f.
6-Acetoxymethyl-4-chloro-1-(4,4,4-trifluoro-n-butyl)-1H-pyrazolo[3,4-b]pyridine-5-carboxylic acid ethyl ester (Formula (VIII), $R^1$=$(CH_2)_3CF_3$, $R^3$=H, X=Cl, R=$CH_2CH_3$, $R^{11}$=$CH_3$, $R^7$=H, $R^8$=H)

The title compound was prepared according to the procedure of Example 19c. using the 1-trifluorobutyl compound prepared in above Example 45e. instead of the 1-(3-methyl-n-butyl) compound. The acetoxy compound was obtained as a yellow oil; tlc, $R_f$=0.5, silica gel, ethyl acetate:hexane, (1:3).

g.
4-Amino-1,7-dihydro-1-(4,4,4-trifluoro-n-butyl)-5H-furo[3,4-b]pyrazolo[4,3-e]pyridin-5-one (Formula (I), $R^1$=$(CH_2)_3CF_3$, $R^3$=H, $R^4$=H, D=O, n=1, $R^7$=H, $R^8$=H)

The title compound was prepared according to the procedure of Example 19d. using the 1-trifluorobutyl compound prepared in above Example 45f. in place of the 1-(3-methylbutyl) compound. The lactone was obtained as white crystals, mp=196°-197.5° C.; tlc, $R_f$=0.2, silica gel, ethyl acetate:hexane (1:3).

EXAMPLE 46

4-Amino-6,7-dihydro-1-(4,4,4-trifluoro-n-butyl)-6-n-propylpyrazolo[3,4-b]pyrrolo[3,4-e]pyridin-5(1H)-one (Formula (I), $R^1$=$(CH_2)_3CF_3$, $R^3$=H, $R^4$=H, D=$NR^6$, $R^6$=$CH_2CH_2CH_3$, n=1, $R^7$=H, $R^8$=H)

The title compound was prepared according to the procedure of Example 20 using the 1-(4,4,4-trifluorobutyl) compound prepared in Example 45g. instead of the 1-(3-methyl-n-butyl) compound. The lactam was obtained as a white solid, mp=161°-162° C.; tlc, $R_f$=0.2, silica gel, ethyl acetate:hexane (1:1).

Elemental Analysis Calculated for $C_{15}H_{18}N_5F_3O$: C, 52.78; H, 5.31; N, 20.52; Found: C, 52.72; H, 5.31; N, 20.39.

EXAMPLE 47

4-Amino-6-(4-chlorophenyl)-6,7-dihydro-1-n-pentyl-pyrazolo[3,4-b]pyrrolo[3,4-e]pyridin-5(1H)-one (Formula (I), $R^1$=n-pentyl, $R^3$=H, $R^4$=H, D=$NR^6$, $R^6$=$C_6H_4$-p-Cl, n=1, $R^7$=H, $R^8$=H)

A mixture of 1.0 g (3.84 mM) of the lactone prepared in Example 1f., 4.8 g (38 mM) of p-chloroaniline and 10 mg, (0.1 mM) of pyridine hydrochloride was heated at 185° C. for 18 hours. The excess p-chloroaniline was then removed by distillation and the residue chromatographed on 300 ml of silica gel using ethyl acetate/chloroform (1:3) as the eluant to give 0.28 g of the desired lactam, mp=184°-185° C.; MS, m/e=369.

Elemental Analysis Calculated for $C_{19}H_{21}N_5OCl$: C, 61.70; H, 5.45; N, 18.94; Found: C, 61.41; H, 5.59; N, 18.68.

EXAMPLE 48

4-Amino-6-(3-chlorophenyl)-6,7-dihydro-1-n-pentyl-pyrazolo[3,4-b]pyrrolo[3,4-e]pyridine-5(1H)-one (Formula (I), $R^1$=n-pentyl, $R^3$=H, $R^4$=H, D=$NR^6$, $R^6$=$C_6H_4$-m-Cl, n=1, $R^7$=H, $R^8$=H)

A mixture of 1.0 g (3.84 mM) of the lactone prepared in Example 1f., 7.5 g (59 mM) of m-chloroaniline and 10 mg (0.1 mM) of pyridine hydrochloride was heated at 185° C. for 48 hours. The excess m-chloroaniline was removed by distillation and the residue chromatographed on 350 ml of silica gel using ethyl acetate/chloroform (1:4) as the eluant to give 0.3 g of the desired lactam, mp=178.5°-179° C.; MS, m/e=369.

Elemental Analysis Calculated for $C_{19}H_{21}N_5OCl$: C, 61.70; H, 5.45; N, 18.94; Found: C, 61.87; H, 5.47; N, 18.88.

EXAMPLE 49

4-Amino-6,7-dihydro-6-(4-methoxyphenyl)-1-n-pentylpyrazolo[3,4b]pyrrolo[3,4-e]pyridin-5(1H)-one (Formula (I), $R^1$=n-pentyl, $R^3$=H, $R^4$=H, D=$NR^6$, $R^6$=$C_6H_4$-p-$OCH_3$, n=1, $R^7$=H, $R^8$=H)

A mixture of 1.0 g (3.84 mM) of the lactone prepared in Example 1f., 3.71 g (30.2 mM) of p-anisidine and 10 mg (0.1 mM) of pyridine hydrochloride was heated to 185° C. for 18 hours. The excess p-anisidine was then removed by distillation and the residue chromatographed on silica gel using ethyl acetate/chloroform (1:1) as the eluant. The impure lactam was recrystalized from chloroform to give 2 crops of product. Each crop was washed twice with hot ether and then combined to give 0.70 g of pure lactam. The products from a number of similar runs were combined and recrystalized from chloroform to give an analytically pure sample of lactam, mp=222°-223° C.; MS, m/e=365.

Elemental Analysis Calculated for $C_{20}H_{23}N_5O_2$: C, 65.74; H, 6.34; N, 19.16; Found: C, 65.52; H, 6.48; N, 18.87.

EXAMPLE 50

4-Amino-6-(2-chlorobenzyl)-6,7-dihydro-1-n-pentylpyrazolo[3,4-b]pyrrolo[3,4-e]pyridin-5(1H)-one (Formula (I), $R^1$=n-pentyl, $R^3$=H, $R^4$=H, D=$NR^6$, $R^6$=$CH_2C_6H_4$-o-Cl, n=1, $R^7$=H, $R^8$=H)

2.0 g (7.7 mM) of the lactam prepared in Example 15 were added to a stirred suspension of 0.20 g (8.5 mM) of sodium hydride in 60 ml of anhydrous THF under a nitrogen atmosphere. The resulting mixture was stirred at 50° C. for 1 hour, then cooled to room temperature. 1.58 g (7.7 mM) of 2-chlorobenzyl chloride were added dropwise to the mixture which was then stirred at room temperature overnight, then poured into water and extracted with ethyl acetate. The combined extracts were dried over sodium sulfate, filtered and concentrated to leave a yellow solid, which was chromatographed over silica gel using ethyl acetate:hexane (1:1) as the eluant. The fractions containing the desired material were combined and concentrated to give 1.04 g of material which was recrystallized from toluene/hexane to give the title compound as a yellow powder, mp=159°-160° C.; tlc, $R_f$=0.35, silica gel, ethyl acetate:hexane (1:1); MS, m/e=383.

Elemental Analysis Calculated for $C_{20}H_{22}N_5OCl$: C, 62.57; H, 5.78; N, 18.25; Found: C, 62.78; H, 5.96; N, 17.95.

EXAMPLE 51

4-Amino-6,7-dihydro-6-(2-hydroxypropyl)-1-n-pentylpyrazolo[3,4-b]pyrrolo[3,4-e]pyridin-5(1H)-one (Formula (I), $R^1$=n-pentyl, $R^3$=H, $R^4$=H, D=$NR^6$, $R^6$=$CH_2CH(OH)CH_3$, n=1, $R^7$=H, $R^8$=H)

The procedure of Example 23 was followed with 1.2 g (4.6 mM) of the lactone prepared in Example 1f. and 8.9 ml of 2-hydroxypropylamine as the starting materials. The solution was heated in a sealed stainless steel pressure vessel at 185°-200° C. for 15 hours and then concentrated to leave a tan solid which was recrystalized from methanol/water to give 0.6 g of the desired lactam as a beige solid, mp=193°-194° C.; tlc, $R_f$=0.15, silica gel, ethyl acetate; MS, m/e=317.

Elemental Analysis Calculated for $C_{16}H_{23}N_5O_2$: C, 60.55; H, 7.30; N, 22.07; Found: C, 59.96; H, 7.22; N, 22.02.

EXAMPLE 52

This example provides an alternative synthesis for the product of Example 5.

a. 5-Amino-4-cyano-1-(n-pentyl)pyrazole (Formula (XIII), $R^1$=n-pentyl, $R^3$=H)

A warm solution of 6.02 g (49.3 mM) ethoxymethylenemalononitrile in 20 ml of ethanol was added via a cannula to a stirred solution of 6.04 g (59.1 mM)n-pentylhydrazine in 20 ml of ethanol at 50° C. The reaction mixture was then heated to reflux for 30 minutes, then cooled in a refrigerator for 18 hours. The off-white crystalline precipitate was filtered to yield 7.73 g (88%) of the title compound, mp=143°-144° C.; tlc, $R_f$=0.5, silica gel, methanol:chloroform (1:19).

b. Ethyl N-(n-propyl)glycinate 5.53 ml (50 mM) of ethyl bromoacetate were added dropwise to a solution of 20.5 ml (250 mM) of n-propylamine in 50 ml of $CH_2Cl_2$ at 0°. The reaction mixture was then warmed to room temperature and stirred for 1 hour, then concentrated to remove volatiles through a short path distillation head at atmospheric pressure. The residual liquid was taken up in ether and washed with saturated aqueous $NaHCO_3$. The layers were separated and the ether layer was washed once with brine then dried over anhydrous $MgSO_4$. The ether was removed to yield 7.16 g of ethyl N-(n-propyl)-glycinate as a pale yellow liquid.

c. Ethyl N-(ethoxycarbonylacetyl)-N-(n-propyl)glycinate 7.16 g (49.4 mM) of ethyl N-(n-propyl)glycinate and 6.4 ml (50 mM) of ethyl malonyl chloride were added simultaneously to an ice-cold solution of 6.9 g (50 mM) of potassium carbonate in 15 ml water overlaid with 50 ml ether. The cooling bath was removed and the reaction warmed to ambient temperature stirring for 1.5 hours. The aqueous phase was acidified to pH 4 with concentrated HCl and the layers separated. The aqueous phase was extracted with 15 ml ether and the combined ether layer washed with brine and dried over anhydrous $Na_2SO_4$ then concentrated to yield 11.8 g of the desired product as a pale yellow oil.

d. 1-(n-Propyl)-3-carbomethoxy-2,4-pyrrolidione or (Methyl 4-hydroxy-1-(n-propyl)-2-oxo-delta$^3$-pyrroline-3-carboxalate)

9.8 g (37.9 mM) of the product of Example 52c. in 200 ml toluene were added dropwise to a freshly prepared solution of 36.5 mM of sodium methoxide prepared by dissolving 0.84 g sodium metal in 35 ml dry methanol. The solution was stirred and heated to 90° C. for 5 hours. The mixture was cooled to ambient temperature, 25 ml of water were added and the layers separated. The organic phase was extracted with 5 ml water and the combined aqueous layers washed once with ether. The aqueous layer was acidified to pH 1 with concentrated HCl then extracted with methylene chloride three times, each 50 ml. The organic extract were dried over Na$_2$SO$_4$ and then concentrated to afford a yellow solid which was recrystallized from ethyl acetate to give 4.03 g of the title compound as a white solid, mp=124°–128° C.

e. 1-(n-Propyl)-2,4-pyrrolidione (Formula (XIV), D=NR$^6$, R$^6$=CH$_2$CH$_2$CH$_3$, n=1, R$^7$=H, R$^8$=H)

A suspension of 0.70 g (3.29 mM) of the pyrrolidione product of Example 52d. in 150 ml acetonitrile was heated at reflux for 2 hours. The resulting solution was concentrated and the residual oil triturated with ether to leave 0.283 g of the desired product as a white solid; tlc, R$_f$=0.5, silica gel, (1:19) methanol:chloroform.

f. 5-[N-(n-Propyl)-2-oxo-3-pyrrolin-4-yl]amino-1-(n-pentyl)-4-cyanopyrazole (Formula (XV), R$^1$=n-pentyl, R$^3$=H, D=NR$^6$, R$^6$=CH$_2$CH$_2$CH$_3$, n=1, R$^7$=H, R$^8$=H)

A mixture of 0.144 g (1.13 mM) of the pyrrolidione product of Example 52e., 0.21 g (1.20 mM) of the pyrazole product of Example 52a., and a small crystal of para-toluenesulfonic acid monohydrate in 5 ml toluene was heated at gentle reflux for 2 hours. The solution was cooled, then treated sequentially with saturated aqueous Na$_2$CO$_3$ and brine, then dried over anhydrous MgSO$_4$. Filtration through a short plug of 5 g silica gel with 50% ethyl acetate/hexane then 5% methanol/methylene chloride as eluant removed some unreacted pyrazole and gave the product as a white solid; tlc, R$_f$=0.35, silica gel, (1:19) methanol:chloroform.

g. 4-Amino-6,7-dihydro-1-n-pentyl-6-n-propyl-pyrazolo[3,4-b]pyrrolo[3,4-e]pyridin 5(1H)-one (Formula (I), R$^1$=n-pentyl, R$^3$=H, R$^4$=H, D=NR$^6$, R$^6$=CH$_2$CH$_2$CH$_3$, n=1, R$^7$=H, R$^8$=H)

A solution product of Example 52f. in 3 ml CH$_2$Cl$_2$ was added to 10 g (73.4 mM) of zinc chloride which had been dried at 200° C. under high vacuum for 3 hours. The mixture was stirred mechanically and heated slowly to 180° C. under a stream of dry N$_2$ to remove CH$_2$Cl$_2$. The reaction was kept 1 hour at 180° C. then cooled. Water was added, followed by a mixture of CH$_2$Cl$_2$ and THF. The layers were separated and the aqueous phase basified to pH 10 with 20% aqueous NaOH. Sufficient citric acid was added to dissolve the precipitated Zn(OH)$_2$ and the solution was extracted twice with CH$_2$Cl$_2$. The combined organic layers were washed with aqueous basic citrate followed by brine, then dried over anhydrous Na$_2$SO$_4$. The solvents were removed and the resulting solid recrystallized from tert-butyl methyl ether/hexane to afford 60.4 mg of product as fine white needles, mp=145.5°–146.5° C. Tlc and $^1$H NMR data confirmed that the product was identical to that prepared in Example 5.

EXAMPLE 53 a. 5-(Delta$^4$-2-piperidon-4-yl)amino-1-(n-pentyl)-4-cyanopyrazole (Formula (XV), R$^1$=n-pentyl, R$^3$=H, D=NR$^6$, R$^6$=H, n=2, R$^7$=H, R$^8$=H)

The title compound was prepared according to the procedure of Example 52f. using the pyrazole product of Example 52a. and 4-keto-2-piperidone prepared as disclosed in the S. Toda et al. article, supra, in place of the 1-(1-propyl)-2,4-pyrrolidione. The title enamine was obtained as off-white crystals; mp=201°–202° C.; tlc, R$_f$=0.2, silica gel, methanol:chloroform (1:19).

b. 4-Amino-7,8-dihydro-1-n-pentyl-1H-pyrazolo[3,4-b][1,6]naphthyridin-5(6H)-one (Formula (I), R$^1$=n-pentyl, R$^3$=H, R$^4$=H, D=NR$^6$, R$^6$=H, n=2, R$^7$=H, R$^8$=H)

The title compound was prepared according to the procedure of Example 52g. using the product of Example 53a. in place of the product obtained in Example 52f., with the exception that the enamine was added to the ZnCl$_2$ in solid portions. The title lactam was obtained as off-white crystals; mp=161°–162° C.; tlc, R$_f$=0.3, silica gel, methanol:chloroform (1:19).

Elemental Analysis Calculated for C$_{14}$H$_{19}$N$_5$O: C, 61.52; H, 7.01; N, 25.62; Found: C, 61.43; H, 6.94; N, 25.32.

What is claimed is:

1. A pyrazolopyridine compound of a formula selected from the group consisting of the following formulae (VII), (VIII), (XIIA), (XVI) and (XVII):

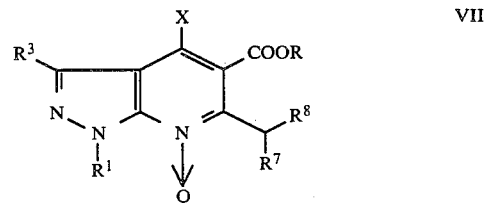

VII

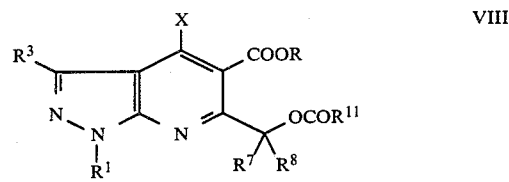

VIII

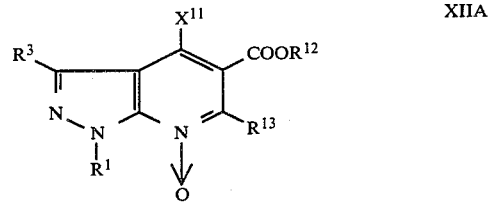

XIIA

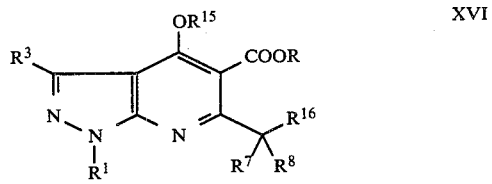

XVI

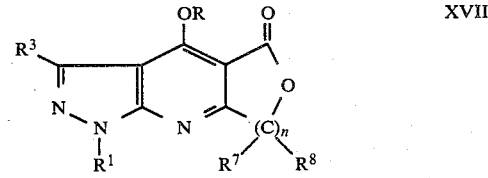

XVII wherein:
R is lower alkyl;

R¹ is straight or branched chain alkyl of about 1 to 10 carbons; straight or branched chain alkyl of about 1 to 10 carbons independently substituted by 1 or 2 of hydroxy, alkoxy of about 1 to 6 carbons or oxo or such an alkyl group substituted by at least one halogen; cycloalkyl of about 3 to 8 carbons; cycloalkylalkyl of about 4 to 12 carbons; akenyl or alkynyl of about 3 to 10 carbons; aryl of about 6 to 10 carbons; aryl of about 6 to 10 carbons independently substituted by one or more of halogen, hydroxy, alkyl of about 1 to 6 carbons, fluoro-substituted alkyl of about 1 to 6 carbons or alkoxy of about 1 to 6 carbons; arylalkyl of about 7 to 2 carbons; or (substituted aryl)alkyl of about 6 to 10 carbons in the aryl and about 1 to 4 carbons in the akyl wherein the substitution is independently one or more of halogen, hydroxy, alkyl of about 1 to 6 carbons, fluoro-substituted alkyl of about 1 to 6 carbons or alkoxy of about 1 to 6 carbons;

R³ is hydrogen; or straight or branched chain alkyl of about 1 to 6 carbons;

R⁷ and R⁸ are independently hydrogen, straight or branched chain alkyl of about 1 to 6 carbons; aryl of about 6 to 10 carbons; aryl of about 6 to 10 carbons independently substituted by one or more of halogen, hydroxy, alkyl of about 1 to 6 carbons, fluoro-substituted alkyl of about 1 to 6 carbons or alkoxy of about 1 to 6 carbons; arylalkyl of about 7 to 12 carbons; or (substituted aryl)alkyl of about 6 to 10 carbons in the aryl and about 1 to 4 carbons in the alkyl wherein the substitution is independently one or more of halogen, hydroxy, alkyl of about 1 to 6 carbons, fluoro-substituted alkyl of about 1 to 6 carbons or alkoxy of about 1 to 6 carbons;

R¹¹ is alkyl of about 1 to 12 carbon atoms;
R¹² is alkyl of about 1 to 6 carbon atoms;
R¹³ is hydrogen;
R¹⁵ is alkyl of about 1 to 6 carbon atoms;
R¹⁶ is —COOH or —CR⁷R⁸OH;
X is chloro or bromo; and
X¹¹ is alkoxy of about 1 to 6 carbon atoms.

2. A compound according to claim 1 having the following formula VII:

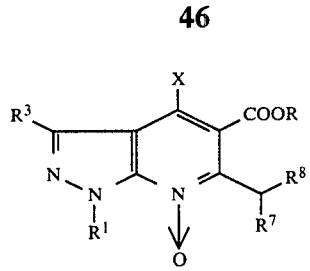

3. A compound according to claim 1 having the following formula VIII:

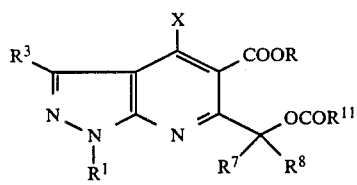

4. A compound according to claim 1 having the following formula XIIA:

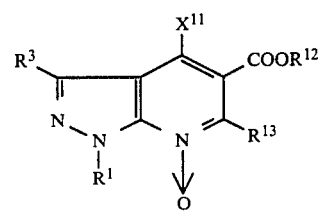

5. A compound according to claim 1 having the following formula XVI:

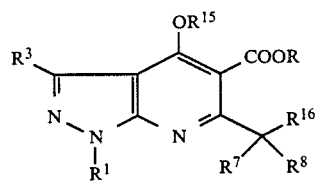

6. A compound according to claim 1 having the following formula XVII:

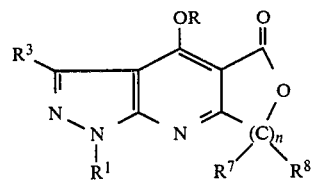

* * * * *

UNITED STATES PATENT AND TRADEMARK OFFICE
CERTIFICATE OF CORRECTION

PATENT NO. : 4,645,838

DATED : FEBRUARY 24, 1987

INVENTOR(S) : BARE ET AL

It is certified that error appears in the above-identified patent and that said Letters Patent is hereby corrected as shown below:

In The Specification:

Column 2, line 53, "$R^{17}$ and are" should read --$R^{17}$ and $R^{18}$ are--.

Column 7, line 11, "lactum" should read --lactam--.

Column 9, line 3, "wherein X is" should read --wherein $X^1$ is--.

Column 9, line 20, "formula to" should read --formula $R^7R^8C(O)CR^7R^8$ to--.

Column 11, line 34, "wherein is" should read --wherein $R^{16}$ is--.

Column 11, line 34, "reagent or if" should read --reagent or $-CR^7R^8OH$ if--.

Example 1, column 16, line 49, "separat.e" should read --separate--.

Example 19, column 24, line 38, "$R^1=_2CH_2CH(CH_3)_2$," should read --$R^1=CH_2CH_2CH(CH_3)_2$,--.

Example 20, column 24, line 58, "$R_1=CH_2CH_2CH(CH_3)_2$," should read --$R^1=CH_2CH_2CH(CH_3)_2$,--.

UNITED STATES PATENT AND TRADEMARK OFFICE
CERTIFICATE OF CORRECTION

PATENT NO. : 4,645,838

DATED : FEBRUARY 24, 1987

INVENTOR(S) : BARE ET AL

It is certified that error appears in the above-identified patent and that said Letters Patent is hereby corrected as shown below:

Example 24, column 27, line 23, "$C_{21}H_{25}N_5O$:" should read --$C_{21}H_{25}N_5O_2$:--.

Example 27, column 28, line 6, "$R^6=CH_2C_6H_2-m-Cl$," should read --$R^6=CH_2C_6H_4-m-Cl$,--.

Example 30, column 29, line 17, "$C_{16}H_{23}N_5O$:" should read --$C_{16}H_{23}N_5O_2$:--.

Example 31, column 30, line 66, "$C_{14}H_{18}H_4O_2$: should read --$C_{14}H_{18}N_4O_2$:--.

Example 34, column 31, line 53, "[3,4b]" should read --[3,4-b]--.

Example 36, column 32, line 35, "N2" should read --$N_2$--.

Example 38, column 35, line 54, "4-Maino-1," should read --4-Amino-1,--.

Example 39, column 36, line 10, "Example 38b" should be deleted.

Example 39, column 36, line 12, "in (0.70g," should read --in Example 38b (0.70g,--

Example 40, column 36, line 33, "pyridin-5(1=H)-one" should read --pyridin-5(1H)-one--.

UNITED STATES PATENT AND TRADEMARK OFFICE
CERTIFICATE OF CORRECTION

PATENT NO. : 4,645,838

DATED : FEBRUARY 24, 1987

INVENTOR(S) : BARE ET AL

It is certified that error appears in the above-identified patent and that said Letters Patent is hereby corrected as shown below:

In The Claims:

Claim 1, column 45, line 16, "7 to 2" should read --7 to 12--.

Signed and Sealed this

Twelfth Day of September, 1989

Attest:

DONALD J. QUIGG

*Attesting Officer*   *Commissioner of Patents and Trademarks*